(12) United States Patent
Fan et al.

(10) Patent No.: US 11,141,496 B2
(45) Date of Patent: Oct. 12, 2021

(54) USE OF BERBERINE OR DERIVATIVE THEREOF IN PREPARING MYOCARDIAL PERFUSION IMAGING AGENT

(71) Applicant: WEST CHINA HOSPITAL, SICHUAN UNIVERSITY, Sichuan (CN)

(72) Inventors: Chengzhong Fan, Sichuan (CN); Xiaoai Wu, Sichuan (CN); Meng Liang, Sichuan (CN); Xiaoli Mei, Sichuan (CN); Tong Zhang, Sichuan (CN); Rang Wang, Sichuan (CN); Haotian Chen, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 0 days.

(21) Appl. No.: 16/619,884

(22) PCT Filed: Jun. 7, 2018

(86) PCT No.: PCT/CN2018/090295
§ 371 (c)(1),
(2) Date: May 11, 2020

(87) PCT Pub. No.: WO2018/224016
PCT Pub. Date: Dec. 13, 2018

(65) Prior Publication Data
US 2020/0330622 A1    Oct. 22, 2020

(30) Foreign Application Priority Data
Jun. 9, 2017    (CN) .......................... 201710433089.4

(51) Int. Cl.
A61K 51/00    (2006.01)
A61M 36/14    (2006.01)
A61K 51/04    (2006.01)

(52) U.S. Cl.
CPC ................ *A61K 51/0455* (2013.01)

(58) Field of Classification Search
CPC .................................................. A61K 51/0455
USPC ......................................................... 424/1.89
See application file for complete search history.

(56) References Cited

U.S. PATENT DOCUMENTS

| | | | |
|---|---|---|---|
| 2004/0033197 A1* | 2/2004 | Madar | A61B 6/507 424/9.1 |
| 2015/0132222 A1* | 5/2015 | Conti | A61B 6/503 424/1.77 |

FOREIGN PATENT DOCUMENTS

| | | | |
|---|---|---|---|
| CN | 101816653 A | | 9/2010 |
| CN | 102989017 A | * | 3/2013 |
| CN | 102989017 A | | 3/2013 |
| CN | 107233585 A | | 10/2017 |

OTHER PUBLICATIONS

Diogo et al. Curr. Drug Targets, 2011, 12, 850-859. (Year: 2011).*
Mikes et al. Biochim. Biophys. Acta. 1983, 723, 231-239. (Year: 1983).*
Liang J. Nucl. Med. 2017, 58 (supp. 1), 162 (Year: 2017).*
Mei, Xiaoli et al.; 18F-Berberine Derivatives: a Potential Molecular imaging Agent for Tumor Targeting by PET/CT Tumor; Journal of Biomedical Engineering; Apr. 30, 2015, vol. 32, No. 2.

* cited by examiner

*Primary Examiner* — Michael G. Hartley
*Assistant Examiner* — Sean R Donohue
(74) *Attorney, Agent, or Firm* — Novick, Kim & Lee, PLLC; Allen Xue

(57) ABSTRACT

Berberine or its derivatives are used in the preparation of myocardial perfusion imaging agents It has been verified using in vitro investigations, in vivo biodistribution, and small animal PET dynamic imaging, etc., that $^{18}$F-labeled berberine derivatives can specifically accumulate in cardiomyocytes or heart tissues, and has good distribution properties of targetting heart muscle in living animals, together with high contrast values of heart v.s. peripheral tissue (liver, lung, blood, muscle, bone, etc.).

4 Claims, 16 Drawing Sheets

USE OF BERBERINE OR DERIVATIVE THEREOF IN PREPARING MYOCARDIAL PERFUSION IMAGING AGENT

TECHNICAL FIELD

The present invention belongs to the field of medical diagnosis, and particularly relates to the use of berberine or its derivatives in the preparation of myocardial perfusion imaging agents.

BACKGROUND ART

Coronary heart disease is one of the main diseases that endanger human survival and health. Statistical data show that the incidence and mortality of coronary heart disease in China have been increasing year by year, and it has a trend of younger. This is not only the patient's injury, but also brings heavy economic burden on the family and the society. Since the 1970s, myocardial perfusion imaging has been used for non-invasive diagnosis of heart diseases, and currently, it has become an important imaging method for diagnosing coronary heart disease, assessing its extent and scope, evaluating curative effects, and judging prognosis. Myocardial perfusion imaging is of great significance to guide the treatment of this disease.

Myocardial perfusion imaging is divided into SPECT (single photon emission computed tomography for nuclear medicine) and PET (positron emission computed tomography). Compared with SPECT, PET myocardial perfusion imaging has the advantages of higher spatial resolution, time resolution and more accurate attenuation correction technology, and it has higher sensitivity, and can quantitatively measure the coronary blood flow perfusion. PET has high sensitivity, high specificity, and high accuracy for diagnosis of CAD, and thus has attracted widespread attention from researchers.

At present, PET myocardial perfusion imaging drugs approved by FDA include [$^{15}$O]H$_2$O (half-life 2.06 min), [$^{13}$N]NH$_3$ (half-life 9.96 min), and $^{82}$Rb (half-life 1.25 min), but their half-lives are all too short (<10 min), and they need be produced by on-line cyclotron, thus are unable to perform exercise-gated myocardial perfusion imaging, that have greatly limited the widespread clinical application of PET myocardial perfusion imaging. The physical half-life of $^{18}$F is as long as 109.8 min, which is more suitable for clinical PET imaging, and $^{18}$F is the most commonly used nuclide in clinical practice. $^{18}$F has good nuclear physical and chemical properties and is also the first choice for developing new PET positron drugs. Therefore, the development of new $^{18}$F-labeled myocardial perfusion imaging agents has important practical significance.

Berberine is an isoquinoline alkaloid, which can be isolated from a variety of traditional Chinese herbs such as *Hydrastis canadensis, Cortex phellodendri, Coptis chinensis*, etc. Berberine has a wide range of biological effects, such as antibacterial, anti-inflammatory, antidiarrheal, antiemetic and antipyretic actions, as well as analgesia and so on. Many pharmacological studies at home and abroad have found that berberine has anti-tumor, hypoglycemic, hypolipidemic effects, together with inhibits endothelial cell apoptosis and vascular smooth muscle cell proliferation, regulates the immune system, as well as shows anti-heart failure, anti-arrhythmia, and anti-atherosclerosis properties, etc. Currently, there are no reports on the use of berberine or its derivatives in myocardial perfusion imaging.

Content of the Invention

The object of the present invention is to provide the use of berberine or its derivatives in the preparation of myocardial perfusion imaging agents. The present invention further provides the use of berberine or its derivatives in the preparation of myocardial perfusion imaging agents.

The present invention further provides the use of radiolabeled berberine or its derivatives in the preparation of myocardial perfusion imaging agents.

Radiolabel, i.e. radionuclide labeling.

Wherein, said radiolabel is $^{18}$F-label.

Wherein, the structures of said $^{18}$F-labeled berberine derivatives are:

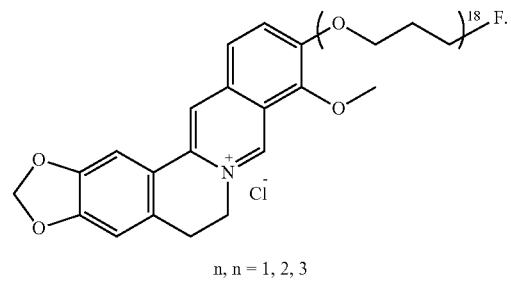

n, n = 1, 2, 3

Wherein, the structures of said $^{18}$F-labeled berberine derivatives are:

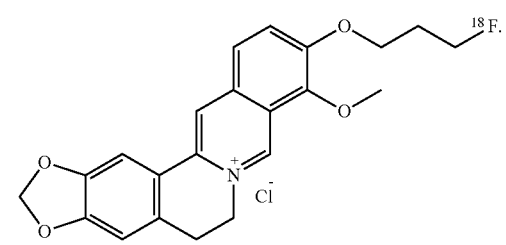

Wherein, said myocardial perfusion imaging agents are positron myocardial perfusion imaging agents. The present invention further provides the use of berberine or its derivatives in the preparation of reagents for diagnosing coronary heart diseases.

The present invention further provides the use of radiolabeled berberine or its derivatives in the preparation of reagents for diagnosing coronary heart diseases, in which said radiolabel is $^{18}$F-label. Wherein, the structures of said $^{18}$F-labeled berberine derivatives are:

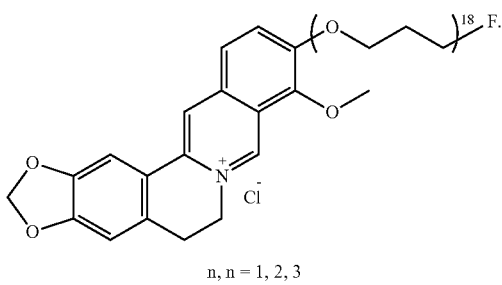

n, n = 1, 2, 3

Wherein, the structures of said $^{18}$F-labeled berberine derivatives are:

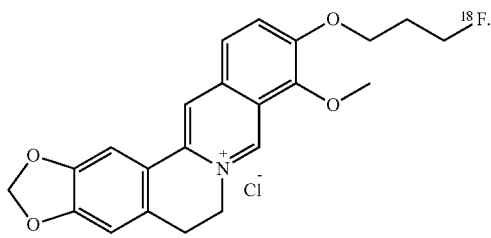

The present invention further provides a method of myocardial perfusion imaging, that uses berberine or its derivatives as imaging agents for myocardial perfusion imaging.

Wherein, said berberine or its derivatives are radiolabeled.

Wherein, said radiolabel is $^{18}$F-label.

Wherein, the structures of said $^{18}$F-labeled berberine derivatives are:

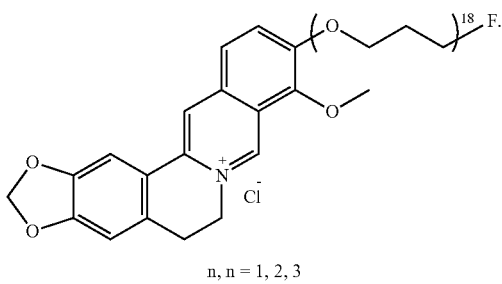

n, n = 1, 2, 3

Wherein, the structures of said $^{18}$F-labeled berberine derivatives are:

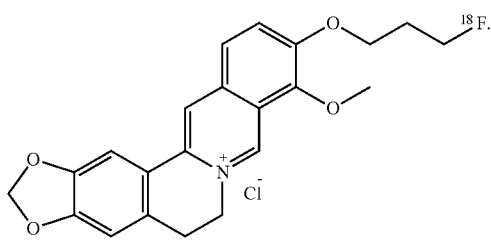

The present invention further provides a method for diagnosing coronary heart diseases, that uses berberine or its derivatives as diagnostic agents for diagnosis.

Wherein, said berberine or its derivatives are radiolabeled.

Wherein, said radiolabel is $^{18}$F-label.

Wherein, the structures of said $^{18}$F-labeled berberine derivatives are:

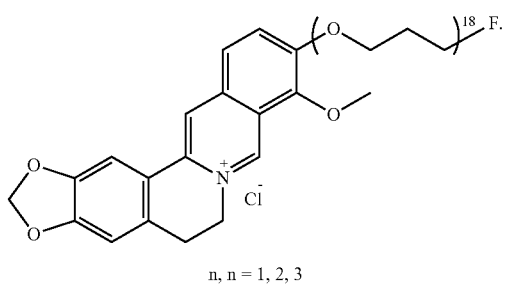

n, n = 1, 2, 3

Wherein, the structures of said $^{18}$F-labeled berberine derivatives are:

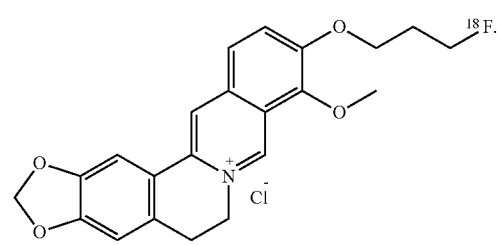

The present invention verifies from in vitro investigations, in vivo biodistribution, and small animal PET dynamic imaging, etc., that $^{18}$F-labeled berberine derivatives according to the present invention can specifically accumulate in cardiomyocytes or heart tissues, and has good distribution properties of targetting heart muscle in living animals, together with high contrast values of heart v.s. peripheral tissue (liver, lung, blood, muscle, bone, etc.), and said compounds can be used as a good PET myocardial perfusion imaging agents for diagnosis of coronary heart disease.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
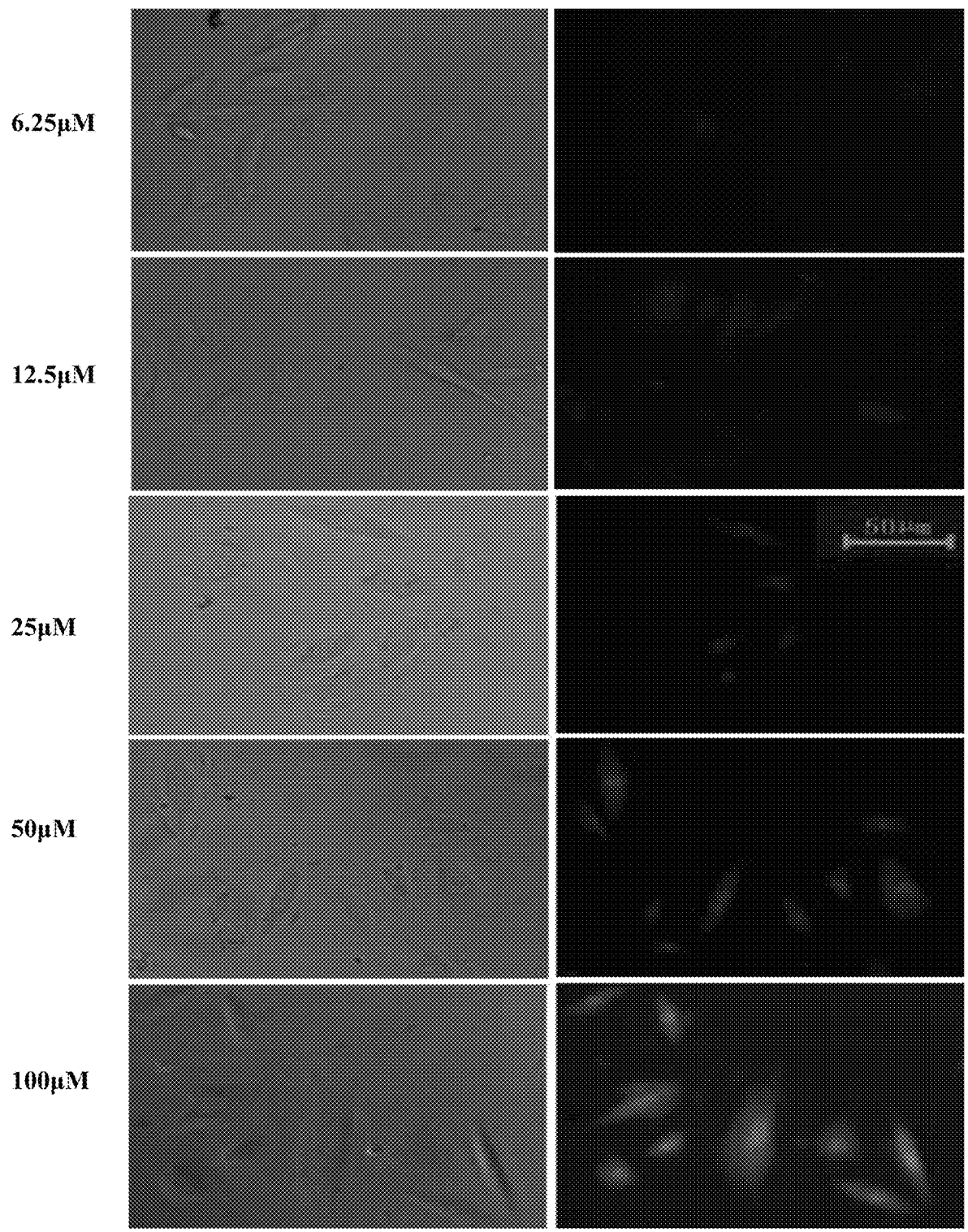
FIG. 1. Fluorescence map of H9C2 cells uptaking [$^{19}$F] HX-01.

Hereinafter, the present invention is further illustrated by examples, but not limited to these examples.

Example 1 Preparation of $^{18}$F-Labeled Berberine Derivatives According to the Present Invention $^{18}$F-labeled berberine derivatives of the present invention (named [$^{18}$F]HX-01) are provided by Department of Nuclear Medicine, West China Hospital, Sichuan University, that can also be synthesized by the method in the patent publication number CN 102989017 B.

[$^{19}$F]HX-01: the non-radioactive reference for $^{18}$F-labeled berberine derivative, that can be synthesized by the method in the patent publication number CN 102989017 B.

Beneficial effects of the present invention are particularly illustrated by following examples.

Experimental Example 1 Cell Uptake Experiment of $^{18}$F-Labeled Berberine Derivative and its Non-Radioactive Reference Substance 1 Materials and Methods 1.1 Cell Lines and Experimental Animals Rat myocardial cells H9C2 and mouse embryonic fibroblasts NIH3T3 were donated by the Regenerative Medicine Research Center of Sichuan University; SD suckling mice were purchased by Chengdu Dashuo Experimental Animal Company from Beijing Slack Biological Co., Ltd.

1.2 Main Reagents

| | |
|---|---|
| DMEM high glucose medium | Hyclone Co., Ltd |
| Dimethylsulfoxide (DMSO) | GIBBO Co., Ltd |
| Calf serum | Sijiqing Biology Co., Ltd |
| Fetal bovine serum | Sijiqing Biology Co., Ltd |
| Penicillin/Streptomycin double antibody | Hyclone Co., Ltd |
| Trypsinase | GIBCO Co., Ltd |
| Collagenase type II | GIBCO Co., Ltd |
| Red fluorescent mitochondrial probe M7513 | Thermo fisher |
| PBS | BOSTER Biological Technology Co., Ltd. |
| CCCP | Shanghai Xinyu Biological Technology Co., Ltd. |

1.3 Apparatus

| Apparatus | Manufacturer |
|---|---|
| YJ-875 S super clean worktable | Suzhou Purification Equipment, China |
| 5% CO$_2$ incubator MCO-175 | SANYO MC0175, Japan |
| Ordinary light microscope ULWCD 0.30 | OLYMPUS CH, Japan |
| −70° C. Low temperature refrigerator | Sanyo Electric Group, Japan |
| Ultra-pure water treatment system | MILLIPORE Company, USA |
| Precision electronic balance ESJ120-4 | Longteng Electronic Co., Ltd, Shenyang, China |
| Microsampler | Eppendorf Company, German |
| Autoclave steamer | Sanyo Electric Group, Japan |
| High-speed centrifuge | Beckman MARCA Company, German |
| Fluorescence microscope | Olympus micropublishe3.3RTV |
| Confocal microscope | THORLABS TiA1, USA |

1.4 Methods 1.4.1 Preparation of [$^{19}$F]HX-01 Stock Solution

An electronic balance was used to weigh the powdery non-radioactive reference [$^{19}$F]HX-01 (3.8 mg) of $^{18}$F-labeled berberine derivative, to which was added 1 ml 50% pre-made DMSO (3 ml DMSO+3 ml three-distilled water), i.e. at concentration of 10 mM ([$^{19}$F]HX-01: 381.7 g/mol). 1 ml solution was taken out and added 9 ml PBS to dilute 10-fold and obtain F-BBR stock solution at concentration of 1 mM, that was stored in a refrigerator at −20° C. for future use.

1.4.2 Culture of Rat Myocardial Cell Lines H9c2 and Mouse Embryonic Fibroblast Cell Lines NIH3T3

The cells were cultured in DMEM medium supplemented with 10% calf serum or fetal bovine serum and 1% penicillin/streptomycin double antibody at 37° C. and 5% $CO_2$ humidified incubator. When the fusion degree reached about 90%, the cells were digested with 0.25% pancreatin and passed on 1:2. The cell morphology and growth were observed with inverted microscope every day, and the culture medium was changed once every 2~3 days. H9c2 cells and NIH3T3 cells were subcultured once every 3~4 days, and the cells in logarithmic growth period were used for the experiment. After more than 20 cell passages, the cells were discarded, and new cells were resuscitated.

1.4.3 Preparation and Culture of Primary Cardiac Myocytes of SD Suckling Mice (1) Preparation of digestive solution: trypsin and type II collagenase were weighed and dissolved in PBS without $Ca^{2+}$ and $Mg^{2+}$ ions, with final concentrations of 0.05% trypsin and 0.05% type II collagenase. The solution was filtered with a filter of 0.22 µm, and prepared prior to use.

(2) Acquisition of heart: 1-3 days newborn SD rats were put into the biosafety cabinet after alcohol disinfection. The chest wall along the left side of the midline of the sternum were cut, and the ophthalmic forceps was used to take ½ of the cardiac apex tissue, that was put into a 10 ml sterile negative pressure bottle containing 3 ml DMEM high sugar medium.

(3) Breaking of heart tissue: the obtained heart tissue was cut into about 1 mm blocks with ophthalmic scissors, washed three times with PBS without $Ca^{2+}$ and $Mg^{2+}$ ions, and the tissue blocks were transferred to 50 ml centrifuge tubes for use.

(4) 5-10 ml Digestion solution was added to the centrifuge tube, mixed and vortexed. The solution was aspirated by a pipette and discarded. Then, 5-10 ml digestive fluid was re-added to digest in 37° C. water bath for about 3-5 min until the digestive fluid appeared cloudy. The supernatant was transferred to a centrifuge tube containing 10 ml termination medium (DMEM high glucose medium+10% calf serum+1% penicillin/streptomycin double antibody).

(5) Step (4) was repeated until no obvious tissue block was observed in the centrifuge tube, i.e. unvisible by naked eyes or having a small amount of flocculent gelatinous precipitate.

(6) The centrifuge tube with the cell suspension was placed in a low-temperature centrifuge and centrifuged at 1400 r for 5 min.

(7) The supernatant was collected, and the cells were resuspended in DMEM high glucose medium containing 10% fetal bovine serum, and pipetted evenly. The collected supernatant was centrifuged again as step (6), and then the supernatant was discarded. All cells were resuspended in DMEM high glucose medium containing 10% fetal bovine serum and blew away.

(8) Differential adherence: the cells were firstly inoculated in a Petri dish and allowed to attach for 30 minutes. Since the attachment rate of fibroblasts is higher than that of cardiomyocytes, fibroblasts in the culture system can be further removed by differential attachment.

(9) The cell suspension was removed from the culture dish, diluted to $2 \times 10^5$ cells/ml, and then seeded in the six-well plate.

(10) After culture for 15 h in a 37° C., 5% $CO_2$ incubator, 0.1 mM BrdU was added.

(11) After 24 hours, the medium was changed, and the cell morphology was observed with an inverted microscope every day. Cardiomyocytes are clustered and rhythmically beaten, and then the medium is changed every 1~2 days for use.

1.4.4 [$^{19}$F]HX-01 Uptake and Localization in H9C2 Cells and Primary Cardiomyocytes of SD Neonatal Rat H9C2 cells were passed to the $6^{th}$ passage and digested with 0.25% trypsin. The cells in the logarithmic growth phase were collected, and the concentration of the cell suspension was adjusted to $1 \times 10^4$/ml, and then inoculated in a six-well plate, with 2 ml for each well. The plate was incubated at 37° C. in 5% $CO_2$ under saturated humidity for 24 h. After the cells adhered to the wall, DMEM high glucose medium in the wells was removed, and PBS (containing 0.5% FBS) with different concentrations of [$^{19}$F] HX-01 (6.25, 12.5, 25, 50 and 100 µM)) was added, 2 ml for well, and each concentration was set 3 replicate wells. Cell control (containing PBS and cells) and blank control (only with PBS, without cells) were included. After incubation at 37 37° C. in 5% $CO_2$ under saturated humidity for 1 h, the liquid in the well was aspirated and discarded, and each well was rinsed three times with PBS. The cells were observed under a fluorescent microscope with an excitation wavelength of 488 nm.

The extraction of primary cardiomyocytes from SD suckling rats is performed as the Method described in section 1.4.3. The suspension of primary myocardial cells of SD suckling mice, that were collected by differential adhesion, was adjusted to the concentration of $20 \times 10^4$/ml, inoculated in a six-well plate, with 2 ml for each well, and then incubated at 37° C. in 5% $CO_2$ under saturated humidity for 24 h. After adherence, the DMEM high glucose medium in each well was aspirated and discarded, and DMEM high glucose medium containing different concentrations of [$^{19}$F] HX-01 (6.25, 12.5, 25, 50 and 100 µM) was added, with 2 ml for each well, and each concentration has three replicate wells. Moreover, a cell control (containing DMEM high glucose medium and cells) and a blank control (only containing DMEM high glucose medium, without cells) were included. after incubation at 37° C. in 5% $CO_2$ under saturated humidity for 1 h, the liquid in each well was aspirated and removed. After the wells were washed three times with PBS, the cells were observed under a confocal fluorescence microscope with an excitation wavelength of 488 nm.

The suspension of primary myocardial cells of SD suckling mice was adjusted to the concentration of $20 \times 10^4$/ml, inoculated in a six-well plate, with 2 ml for each well, and then incubated at 37° C. in 5% $CO_2$ under saturated humidity for 24 h. After adherence, the DMEM high glucose medium in each well was aspirated and discarded, and DMEM high glucose medium containing different concentrations of [$^{19}$F] HX-01 (6.25, 12.5, 25, 50, 100, 150, and 200 µM) was firstly added, with 2 ml for each well, and each concentration has three replicate wells. After incubation at 37° C. in 5% $CO_2$ under saturated humidity for 1 h, the liquid in each well was aspirated and removed. After the wells were washed three times with PBS, DMEM high glucose medium containing 4 µM red fluorescent mitochondrial probe was added, and then the plate was cultured at 37° C. in 5% $CO_2$ under saturated humidity for 10 min. Subsequently, the liquid in each well was aspirated and removed. After the wells were washed three times with PBS, the cells were finally observed under a confocal fluorescence microscope with an excitation wavelength of 488 nm.

1.4.5 Comparing the Characteristics of [$^{18}$F]HX-01 Uptake in Rat Cardiomyocytes H9C2, SD Neonatal Rat Cardiomyocytes and Mouse Fibroblasts NIH3T3, as Well as Whether CCCP Can Inhibit the [$^{18}$F]HX-01 Uptake in Cardiomyocytes CCCP: Carbonyl cyanide m-chlorobenzene {2-[2-(3-Chlorophenyl) hydrazinylyidene] propanedinitrile, CCCP}, a mitochondrial membrane potential inhibitor.

As described in method 1.4.4, the suspension of rat cardiomyocytes H9C2, NIH3T3 cells and SD neonatal rat primary cardiomyocytes was adjusted to the concentration of $20 \times 10^4$/ml, inoculated in a six-well plate, with 2 ml for each well (containing $4 \times 10^5$ cells), and the experimental group and CCCP inhibition group were included, The plate was cultured at 37° C. in 5% $CO_2$ under saturated humidity for 24 h. After the cells adhered, 30 minutes before addition of [$^{18}$F]HX-01, the DMEM high-glucose medium in the Petri dish was aspirated and discarded. DMEM high-glucose medium containing CCCP (0.5 μM) was firstly added at 2 ml/well to the cell culture dish in CCCP inhibition group, while an equal volume of DMEM high-glucose medium without CCCP was added to the cell culture dish in the experimental groups, and the dish was incubated at 37° C. in 5% $CO_2$ under saturated humidity for 30 min. Then, 100 μl solution of [$^{18}$F]HX-01 dissolved in saline was added to each well at a dose of 2.5 μCi. The plate was incubated at 37° C. in 5% $CO_2$ under saturation humidity. After incubation for 5 min, 10 min, 30 min, 60 min and 120 min, the liquid in the well was collected, and rinsed 3 times with PBS, and all the rinse liquid was collected in the radioimmunotubes. After digestion with 0.25% trypsin, all cells were collected in the radioimmunotubes, and the radioactivity counts of the liquid and cells in the wells were measured with a γ counter, and the data were recorded. Three replicate holes were set for each time point.

2 Results 2.1 Localization and Distribution Characteristics of [$^{19}$F]HX-01 in Rat Cardiomyocyte Cell Lines H9C2

Using the spontaneous green fluorescence of [$^{19}$F]HX-01, the uptake of [$^{19}$F]HX-01 in rat myocardial cell lines H9C2 and its localization distribution in cells were observed with an inverted fluorescence microscope. The results are shown in FIG. 1.

It can be seen from FIG. 1: after incubation for 2 h at low concentration of 6.25 μM, no exact fluorescence signal is shown under the microscope; after incubation at lower concentration of 12.5 μM for 2 h, weak green fluorescence appears in H9C2 cells, but the location display is unclear; after incubation for 2 h at 25 μM, there is a visible fluorescence signal in H9C2 cells, and the fluorescence is mainly located in the nucleus; with the increase in drug concentration, after incubation for 2 h at 50 μM, the fluorescence signal in the cell is gradually increased, the nucleus is displayed more clearly, and the green fluorescence signal evenly distributed in the cytoplasm; after incubation for 2 h at high concentration of 100 μM, the fluorescence signal in the nucleus was further enhanced, the fluorescence signal in the cytoplasm was evenly increased, and the fluorescence in the nucleus was significantly higher than that in the cytoplasm.

It can be seen that non-radioactive reference [$^{19}$F]HX-01 of $^{18}$F-labeled berberine derivatives can be taken up by rat myocardial cells, meeting the requirements of myocardial perfusion imaging agent.

2.2 Localization and Distribution Characteristics of [$^{19}$F]HX-01 in Primary SD Cardiomyocytes Using the spontaneous green fluorescence of [$^{19}$F]HX-01, a higher resolution confocal microscope was used to observe the uptake of [$^{19}$F]HX-01 in primary cardiomyocytes of SD neonatal rats, as well as its localization and distribution characteristics. Results are shown in FIG. 2.

Figure 2:
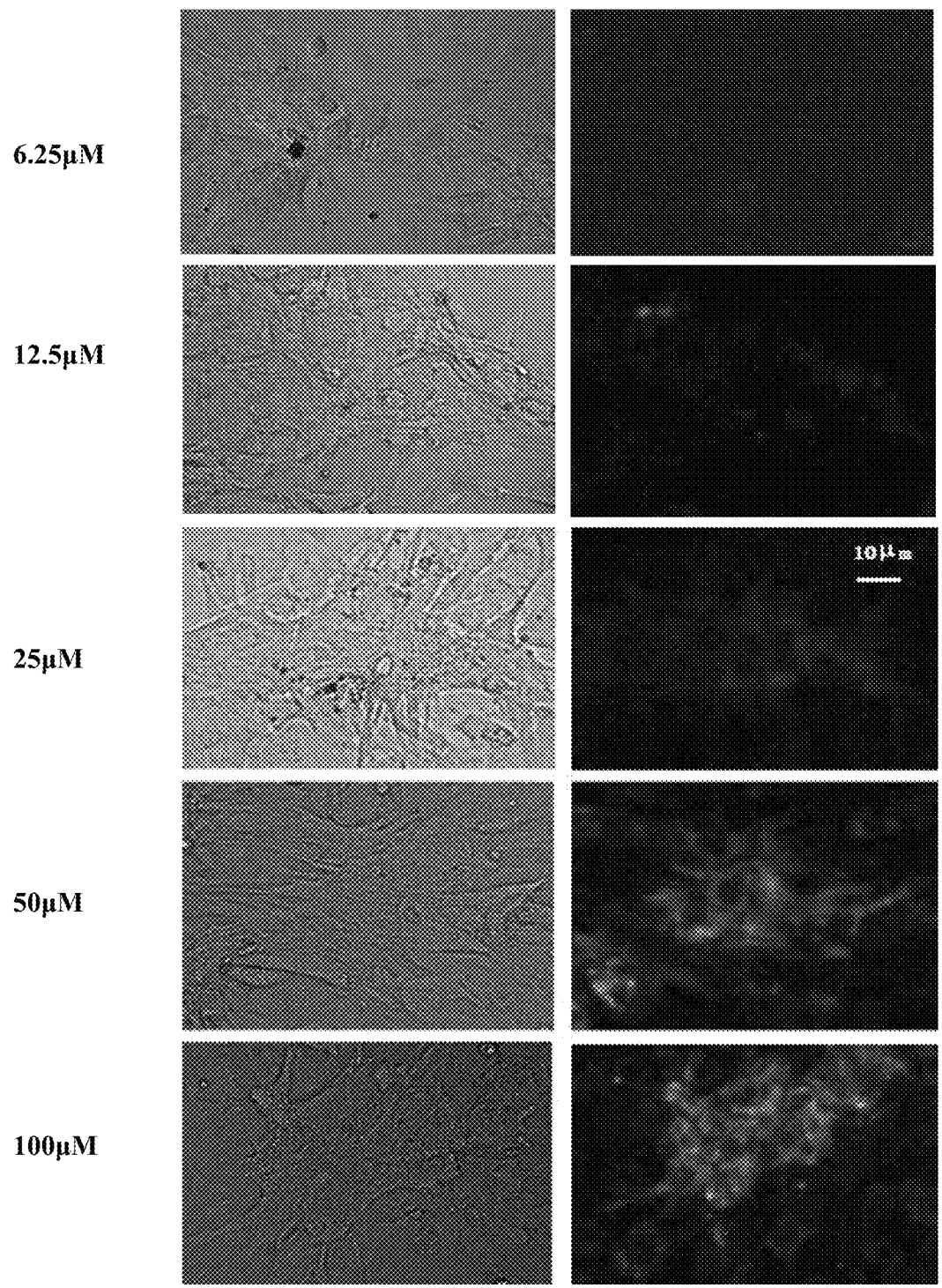
FIG. 2. Fluorescence map of SD suckling rat primary cardiomyocytes uptaking [$^{19}$F]HX-01.

It can be seen from FIG. 2: the distribution of [$^{19}$F]HX-01 in primary cardiomyocytes of SD suckling rats has the following characteristics: after incubation for 2 h at low concentration of 6.25 μM, no exact fluorescent signal is seen under the microscope; after incubation for 2 h at lower concentration of 12.5 μM, a faint fluorescent signal appears in the cytoplasm; after incubation for 2 h at 25 μM, [$^{19}$F]HX-01 was aggregated in the cytoplasm in a granular shape and distributed in a loose granular shape, and there was almost no fluorescence in the nucleus; as the concentration increased, after incubation for 2 h at a higher concentration of 50 μM, the fluorescence intensity in the cytoplasm gradually increased, coarse particles are densely arranged in the cytoplasm, and the distribution is similar to that in mitochondria; after incubation for 2 h at a high concentration of 100 μM, the fluorescent signal in the mitochondria is further enhanced, and a small amount of fluorescence can be seen in the nucleus, indicating part of [$^{19}$F]HX-01 enters the nucleus.

It can be seen that non-radioactive reference [$^{19}$F]HX-01 of $^{18}$F-labeled berberine derivatives can be taken up by primary myocardial cells of SD suckling rats, meeting the requirements of myocardial perfusion imaging agent.

In order to further clarify the localization characteristics of [$^{19}$F]HX-01 in the subcellular organelles of SD rat primary cardiomyocytes, after addition of above different concentrations of [$^{19}$F]HX-01 and incubation for 1 h, the medium was discarded, and each well was rinsed with PBS three times. Each well was added the medium containing mitochondrial specific probe with red fluorescence (Mito Tracker Red (M7513), Thermo fisher) and incubated for another 10 min, the medium was removed, and each well was rinsed with PBS three times. Whether the distribution of spontaneous green fluorescence from [$^{19}$F]HX-01 is consistent with that of red fluorescence produced by mitochondrial-specific probe was observed under confocal microscope. The results are shown in FIG. 3.

Figure 3:
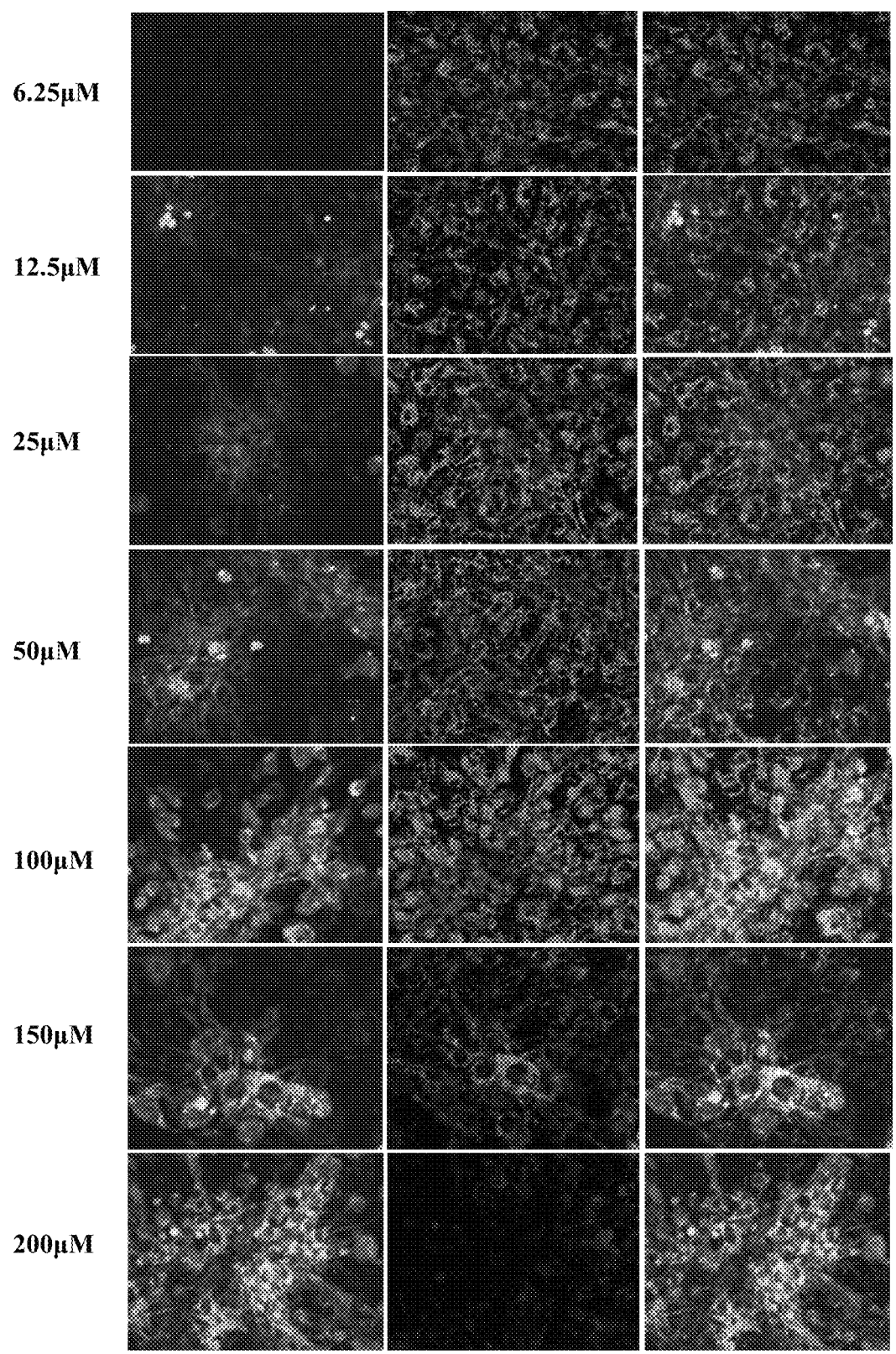
FIG. 3. Fluorescence map of SD suckling rat primary cardiomyocytes uptaking [$^{19}$F]HX-01, with aid of red mitochondrial probe localization.

It can be seen from FIG. 3: First, the green autofluorescence of non-radioactive standard control [$^{19}$F]HX-01 is mainly concentrated in the mitochondria of cardiomyocytes, and no obvious signal of green fluorescence is seen in the surrounding mixed cells (mainly fibroblasts). The intensity of the green fluorescent signal in the mitochondria of cardiomyocytes gradually improved as the increase of [$^{19}$F]HX-01 drug concentration. After the concentration of [$^{19}$F]HX-01 reached 100 μM, as the concentration of [$^{19}$F]HX-01 continually increased, the green fluorescence distribution also appeared in the nucleus of cardiomyocytes, but there was no obvious green fluorescence displayed in the surrounding heterogeneous cells.

Secondly, the red fluorescence of the mitochondrial-specific probe (M7513) appeared in the mitochondria of all cells in a granular distribution. The fluorescence intensity in the mitochondria of cardiomyocytes and that in the mitochondria of the surrounding mixed cells (mainly fibroblasts) did not show significant differences.

Finally, the spontaneous green fluorescent signal of non-radioactive standard control [$^{19}$F]HX-01 at different concentrations was localized in the mitochondria of primary cardiomyocytes of SD neonate rats, that is highly consistent with the location and distribution of red fluorescent signal of the mitochondrial-specific probe (M7513) in the cardiomyocytes. When the concentration of [$^{19}$F]HX-01 was significantly increased, the intensity of green fluorescence in cardiomyocytes gradually increased, while the red fluorescence in mitochondria of cardiomyocytes gradually weakened, indicating that [$^{19}$F]HX-01 can competitively inhibit the entrance of mitochondrial-specific probes (M7513) into the mitochondria of SD neonatal rat primary cardiomyocytes. There is a competitive binding relationship between both of them.

It can be seen that the non-radioactive control [$^{19}$F]HX-01 of $^{18}$F-labeled berberine derivative can be taken up by the primary cardiomyocytes of SD neonatal rats, and is located in the mitochondria of cardiomyocytes, with binding characteristics of targeting cardiomyocytes, meeting the requirements of myocardial perfusion imaging agents.

2.3 Comparing the Uptake Characteristics of [$^{18}$F]HX-01 in Different Cells

Figure 4:
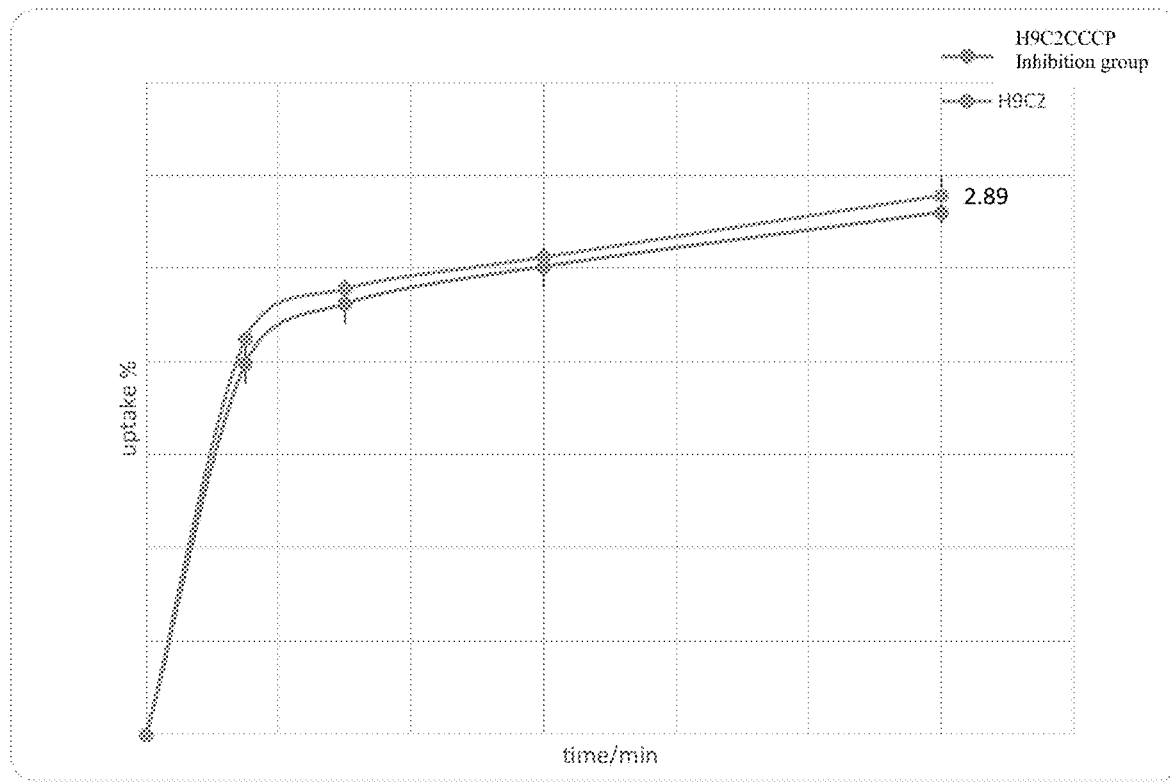
FIG. 4. Time-activity curve of H9C2 cells uptaking [$^{18}$F] HX-01.
Figure 5:
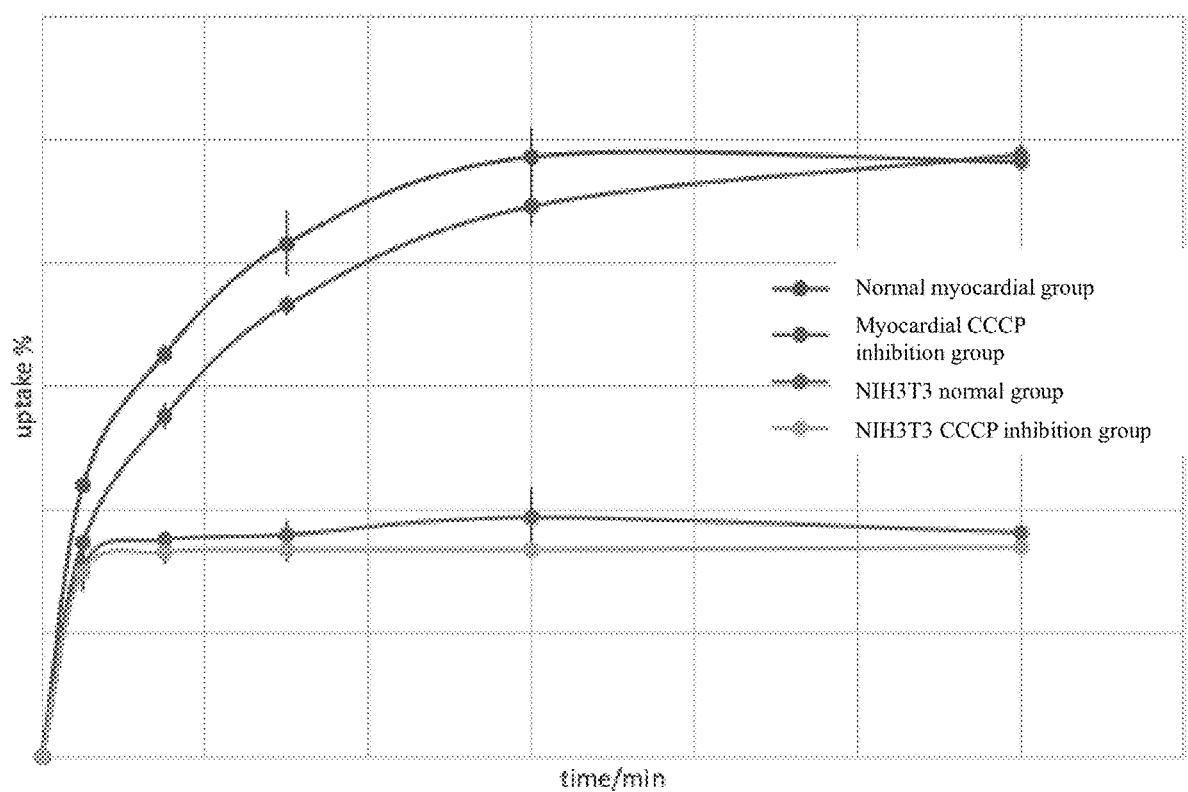
FIG. 5. Time-activity curve of SD suckling rat primary cardiomyocytes and NIH3T3 cells uptaking [$^{18}$F]HX-01.

Results are shown in FIGS. 4-5.

As shown in FIG. 4, the uptake of [$^{18}$F]HX-01 in rat myocardial cells H9C2 cells increased rapidly within 30 min, and slowly increased between 30 min and 120 min, that distributed in a platform. The uptake reached a peak value at 120 min, which was 2.89%±0.11%; while the cells in the control group and CCCP inhibition group didn't show significant difference in the uptake percentage.

As shown in FIG. 5, the uptake of [$^{18}$F]HX-01 in primary cardiomyocytes of SD neonatal rats also showed an obvious increase in the uptake percentage within 30 min, with a uptake percentage of 2.08%±0.13% in 30 minutes, and the percentage slowly increased from 30 min to 120 min. At 120 min, the intake percentage reached a peak value of 2.41%±0.03%. There was no significant difference in the intake percentage between the normal group and the CCCP inhibition group (p>0.05). However, the uptake percentages of [$^{18}$F]HX-01 in mouse fibroblasts NIN3T3 cells were 0.78±0.06 and 0.91±0.01 at 5 min and 120 min, respectively. There was no significant change during the period, and the distribution presents a platform. The normal group and CCCP inhibition group did not show a significant difference (p>0.05).

It can be shown that the uptake of $^{18}$F-labeled berberine derivatives in rat cardiomyocytes and SD neonatal rat primary cardiomyocytes is significantly higher than that in mouse fibroblasts. [$^{18}$F]HX-01 has the characteristics of targeting cardiomyocytes, consistent with the phenomenon of [$^{19}$F]HX-01 specifically distributing in cardiomyocytes. $^{18}$F-labeled berberine derivatives can be used as imaging agents for myocardial perfusion.

Experimental Example 2 Biodistribution of $^{18}$F-Labeled Berberine Derivatives of the Present Invention in Healthy Mice 1 Experimental Materials and Methods
1.1 Experimental Animals Kunming mice used in the experiment were purchased by Chengdu Dashuo Experimental Animal Company from Beijing Slake Biological Co., Ltd. and fed in the Experimental Animal Center of Sichuan University.

1.2 Main Reagents

The target compound fluorine [$^{18}$F]HX-01 with radiochemical purity (RCP) >99% was prepared by Department of Nuclear Medicine, West China Hospital, Sichuan University.

Physiological saline was purchased from West China Hospital of Sichuan University.

1.3 Main Materials

Xinhua No. I paper, insulin needle, and pipette tip (specifications: 1000 µL, 200 µL, 10 µL) were all purchased from Costar Stripette (New York, USA). PE gloves, medical powder-free latex gloves, and masks were all purchased from Kirgen Bioscience (Shanghai, China).

1.4 Main Apparatus

| Apparatus | Manufacturer |
| --- | --- |
| Ultra-pure water treatment system | MILLIPORE Company, USA |
| Precision electronic balance ESJ120-4 | Longteng Electronic Co., Ltd, Shenyang, China |
| Micro sampler | Eppendorf Company, German |
| FC3600 Radioactivity detector | Bioscan Company, USA |
| FJ-202γ Radioimmunocounter | Xi'an State-owned No. 262 Factory, China |

1.5 Experimental Method $^{18}$F-labeled berberine derivative [$^{18}$F]HX-01 with radiochemical purity (RCP) >99% was quantitatively injected to normal Kunming mice via the tail vein, and the mice were sacrificed at 5 min, 10 min, 30 min, 1 h, 2 h and 4 h after injection. Tissue samples of important organs such as blood, heart, lung, liver, kidney, spleen, stomach, small intestine, muscle, bone, brain, etc., were collected, and after weighing, the total radioactivity of each specimen was measured with a γ counter. The radioactive dose percentage per gram of tissue was calculated based on the injected dose (The radioactivity percentage of injected dose per gram of tissue; % ID/g).

Specific operation procedures are as follows:

(1) Experimental animals: healthy Kunming mice, 4-6 weeks old, half female and half male, average weight of about 25 g (25 g±0.5 g).

(2) Radiopharmaceuticals [$^{18}$F]HX-01: the radiochemical purity >99%, the injection dose of about 100 µCi (100 µCi±10 µCi), the volume of about 100 µl. Taking three test tubes and adding 100 µl [$^{18}$F]HX-01 to each tube as a standard source control.

(3) Groups of experimental animals: in the biodistribution test, 30 healthy Kunming mice were randomly divided into 6 groups: 5 min group, 10 min group, 30 min group, 1 h group, 2 h group, and 4 h group, and each group included 4-5 mice, with half male and half female.

(4) Extraction and weighing of important organs and tissues: each mouse was injected with 100 µCi [$^{18}$F]HX-01 (100 µCi±10 µCi) via tail vein, about 100 µl. Test rats were killed by broken neck at 5 min, 10 min, 30 min, 1 h, 2 h and 4 h after injection, respectively, and weighed. The samples of heart, lung, liver, kidney, spleen, stomach, small intestine, muscle, bone, brain, etc., were taken and weighed. The radioactivity count of above sample per minute were measured with the γ radioimmunoassay counter (FJ-202), and then converted into the percentage of the radioactivity dose per gram of tissue based on the injection dose (% ID/g).

(5) Experimental data were represented as mean±standard deviation (x±SD).

(6) Statistical analysis: Paired t test, p value <0.05 indicating statistical significance.

2. Results

Figure 7:
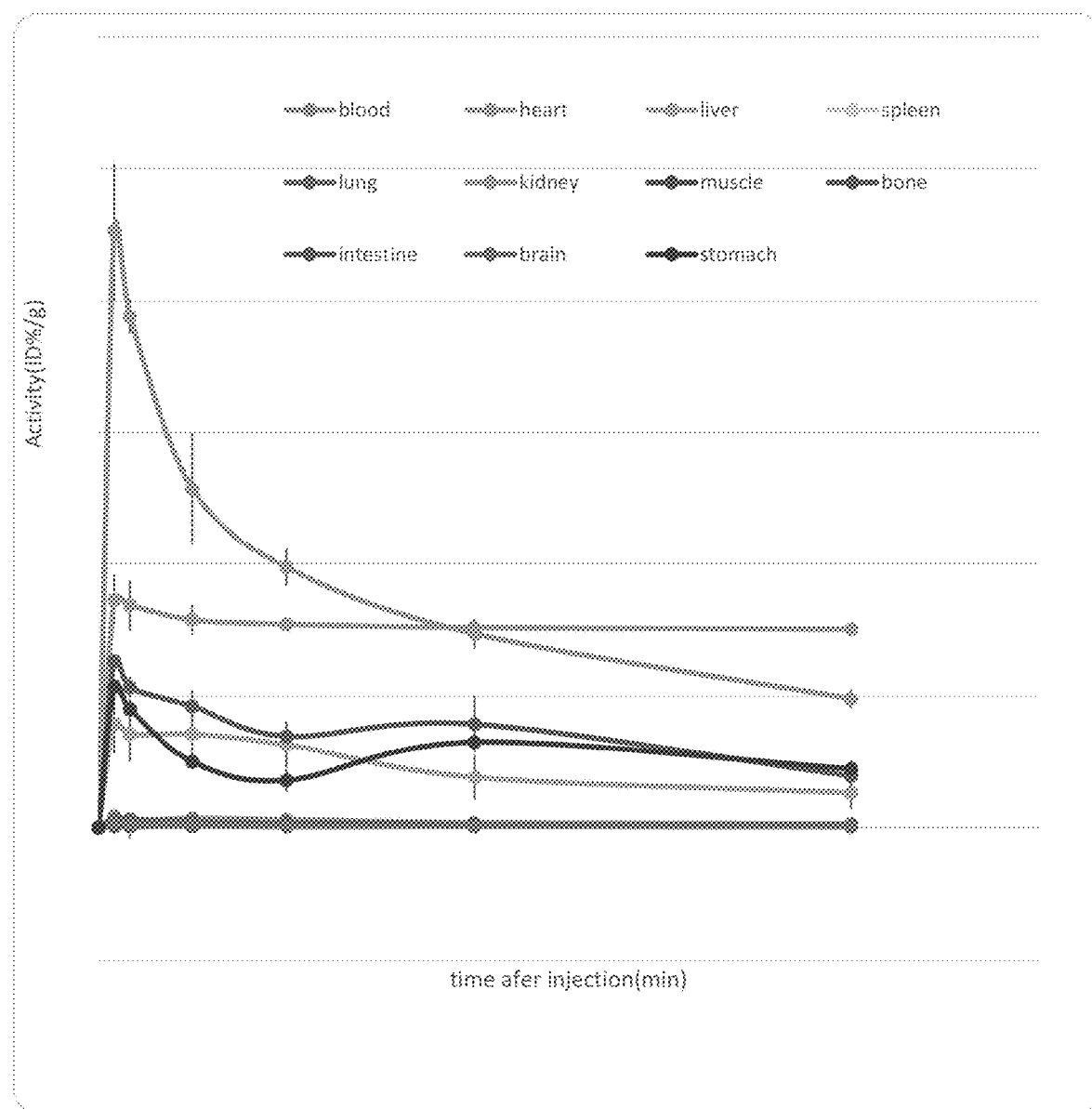
FIG. 7. Time-activity curves of various organs within 4 hours after injection of [$^{18}$F]HX-01 in healthy Kunming mice: the percentage of radioactive material per gram of tissue based on the injection amount (% ID/g).

The radioactive biological distribution of various tissues and organs of healthy Kunming mice is shown in Table 1 and FIG. 7.

TABLE 1

The biodistribution of [$^{18}$F]HX-01 in normal Kunming mice in vivo (% ID/g, x ± SD, n = 4).

| Tissues | 5 min | 10 min | 30 min | 1 h | 2h | 4h |
|---|---|---|---|---|---|---|
| blood | 1.68 ± 0.11 | 1.09 ± 0.08 | 1.37 ± 0.27 | 1.20 ± 0.10 | 0.73 ± 0.27 | 0.55 ± .01 |
| heart | 34.64 ± 3.86 | 33.76 ± 3.81 | 31.55 ± 2.24 | 30.88 ± 0.57 | 30.38 ± 0.2 | 30.12 ± 0.22 |
| liver | 15.88 ± 0.04 | 14.18 ± 0.39 | 14.20 ± 0.31 | 12.61 ± 0.51 | 7.63 ± 1.13 | 5.27 ± 0.97 |
| spleen | 4.75 ± 0.13 | 4.27 ± 0.05 | 4.50 ± 0.30 | 3.57 ± 0.08 | 3.45 ± 0.16 | 2.47 ± 0.05 |
| lung | 1.34 ± 0.11 | 1.24 ± 0.08 | 0.93 ± 0.06 | 0.69 ± 0.06 | 0.5 ± 0.15 | 0.43 ± 0.09 |
| kidney | 90.43 ± 10.55 | 77.59 ± 2.67 | 51.51 ± 8.45 | 39.55 ± 2.85 | 29.44 ± 2.26 | 19.58 ± 1.39 |
| muscle | 0.36 ± 0.03 | 0.36 ± 0.02 | 0.35 ± 0.02 | 0.36 ± 0.02 | 0.37 ± 0.02 | 0.37 ± 0.03 |
| bone | 0.23 ± 0.02 | 0.24 ± 0.02 | 0.23 ± 0.02 | 0.23 ± 0.01 | 0.23 ± 0.01 | 0.24 ± 0.02 |
| intestine | 25.28 ± 0.79 | 21.32 ± 1.55 | 18.45 ± 2.4 | 13.9 ± 1.89 | 15.72 ± 4.32 | 7.84 ± 0.73 |
| brain | 0.7 ± 0.12 | 0.48 ± 0.03 | 0.38 ± 0.09 | 0.22 ± 0.02 | 0.24 ± 0.01 | 0.34 ± 0.02 |
| stomach | 21.48 ± 0.89 | 10.01 ± 1.62 | 17.98 ± 0.23 | 7.17 ± 1.74 | 12.99 ± 0.68 | 8.92 ± 1.28 |

As shown in Table 1 and FIG. 7, 5 minutes after intravenous injection of [$^{18}$F]HX-01, a high radioactivity distribution appeared in heart early: 34.84±3.86 ID %/g, and as the time extended to 4 h after injection, the intake value was 30.12±0.22 ID %/g; the radioactivity in the heart continues to maintain a high level, with only a slight decline within 4 hours; hint: the myocardial uptake of [$^{18}$F]HX-01 is early, and the uptake value is high, as well as the uptake maintained at a high level for a long time.

Figure 6:
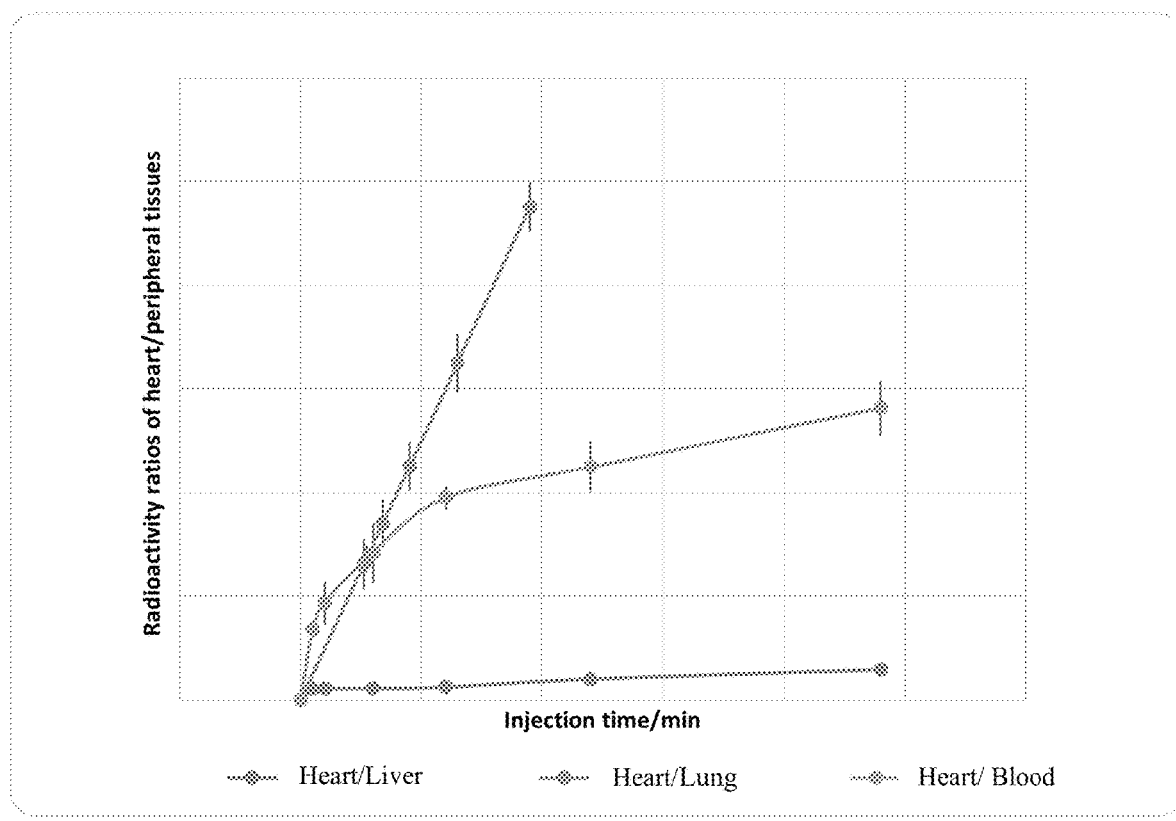
FIG. 6. Change trend graph of radioactivity ratio of heart to surrounding tissues over time.

The radioactivity of liver was higher in the early stage of intake, and then decreased rapidly as the time. The uptake values of [$^{18}$F]HX-01 in liver were 15.88±0.04 ID %/g and 5.27±0.97 ID %/g 5 min and 4 h after injection, respectively. As shown in FIG. 6, the ratio of heart/liver radioactivity was gradually increased, which was 2.18±0.25 and 5.87±1.22 for 5 min and 4 h, respectively, suggesting drug was metabolized in liver.

The radiation uptake value of kidney was the highest, that were 90.43±10.55 and 19.58±1.39 ID %/g 5 minutes and 4 hours after injection, respectively, suggesting that the drug was mainly excreted through kidney.

The distribution of radioactivity in gastrointestinal tract was also high, and as the prolongation of time, the radioactivity distribution also decreased. The radioactivity in stomach and intestines were respectively 8.92±1.28 and 7.84±0.73 till 4 h after injection. It suggested that the drug was excreted not only by kidney, but also by stomach and intestines.

The distribution of radioactivity in the blood was rather low, and 5 minutes after injection the intake value was 1.68±0.11 ID %/g, and the drug was rapidly removed from the plasma. As shown in FIG. 6, for 5 minutes and 4 hours, the radioactivity ratio of heart/blood were 13.58±0.97 and 56.28±5.3, respectively. As the elongation of time, the radioactivity ratio of heart/blood increased significantly, indicating that the plasma protein binding rate of the drug was low.

The uptake of [$^{18}$F]HX-01 in other organs and tissues in the whole body, such as brain, lung, bone, muscle, etc., was extremely low, and as time went on, there was no obvious change in radioactivity distribution; while the radioactivity ratio of heart/peripheral tissues is obviously increased. As shown in FIG. 7, the heart/lung radioactivity ratios were 26.08±4.82 and 94.94±4.71 at 5 min and 4 h, respectively; that suggested that the radioactivity distribution of [$^{18}$F]HX-01 is tissue-specific and has the distribution characteristics of targeting the heart.

As shown, the biodistribution in healthy mice indicated that the uptake of [$^{18}$F]HX-01 by cardiomyocytes is early, and the uptake value is high, and the radioactivity remained at a relatively high level within 4 hours. The uptake of [$^{18}$F]HX-01 by tissues around the myocardium was obviously lower than that by the myocardium (p<0.01), and as the progress of time, the radioactivity of the surrounding tissues gradually decreased. An excellent radioactivity ratio of heart to surrounding tissues such as heart/liver, heart/lung, and heart/blood could be obtained. The drug was mainly metabolized by the liver, mainly excreted by the kidney, and partly excreted through the intestine. The main organs and tissues such as brain, lung, bone, muscle, etc. showed very low drug intake (p<0.01). Therefore, $^{18}$F-labeled berberine derivatives of the present invention had excellent distribution characteristics of targeting myocardial, and could be used as myocardial perfusion imaging agents.

Experimental Example 3 Micro PET Dynamic Imaging of $^{18}$F-Labeled Berberine Derivatives According to the Present Invention in Healthy Rabbits 1 Experimental Materials and Methods 1.1 Experimental Materials 1.1.1 Experimental Reagents

[$^{18}$F]HX-01 was prepared by Department of Nuclear Medicine, West China Hospital, Sichuan University. Physiological saline and chloral hydrate were both purchased from West China Hospital of Sichuan University.

1.1.2 Experimental Animals and Their Feeding Conditions

Name: New Zealand white rabbit

Grade: clean level

Number: three rabbits for each group

Gender: male

Weight range: 2.5±0.2 kg

Source: Chengdu Dashuo Experimental Animal Company purchased from Beijing Slake Biological Co., Ltd.; being raised in the Experimental Animal Center of Sichuan University.

Environmental conditions: noise <60 dB; temperature 20-24° C.; humidity 40%-60%; good ventilation.

Drinking water: the water quality is not lower than the urban drinking water standard.

Feed: full nutrition pellet feed.

1.1.3 Apparatus

| Apparatus | Model | Manufacturer |
| --- | --- | --- |
| Radioactive detector | FC3600 | Bioscan Company, USA |
| PET scanner | GEMINI GXL | Philips Company |
| Precision electronic balance | ESJ120-4 | Longteng Electronic Co., Ltd, Shenyang, China |

1.2 Experimental Method

1.2.1 PET Dynamic Imaging of New Zealand Healthy White Rabbits

The male New Zealand white rabbits (n=3) were placed in a supine position, the limbs were fixed to the rabbit plate with a strap, and 10% chloral hydrate was intraperitoneally injected at a dosage of 3 ml/kg. After successful anesthesia, the ear marginal venous channel was established, and 2 ml saline was first injected through this venous channel, to check whether the venou channel is unobstructed. After confirming the patency, the tracer [$^{18}$F]HX-01 was intravenously injected through the ear marginal venous channel of New Zealand rabbits. Finally, 3 ml saline was injected to wash the tube. The needle was pulled out, the blood was stopped by compression hemostasis, and the injection dose was 0.5 mCi/kg.

Recording image: after intravenous injection of [$^{18}$F]HX-01, CT images from skull base to ankle joint were collected immediately. CT acquisition parameters are 40 mAs, 120 keV, layer thickness 4 mm, layer spacing 4 mm, and matrix 512×512. Then, PET/CT images were collected at the speed of 2 min/bed at the $5^{th}$, $15^{th}$, $30^{th}$, $60^{th}$, $90^{th}$ and $120^{th}$ min, respectively (5 beds). PET image was recorded using 3D acquisition mode. After PET/CT image acquisition, cross-section, sagittal and coronal images were automatically reconstructed by computer. PET image was reconstructed by LOR method after attenuation correction. Meanwhile, PET, CT and PET/CT images were obtained by Syntgra fusion software. Using compassview 5.0 to analyze and process the data, the brain, heart, liver, lung, kidney, bone and muscle of the region of interest (ROI) were drawn on the horizontal axis, and SUVmax was recorded.

1.2.2 Competitive Inhibition Test of [$^{18}$F]HX-01 and its Non-Radioactive Standard [$^{19}$F]HX-01

After anesthesia and fixation, the male New Zealand white rabbits were set as their own control (n=3). On the first day, 2 ml saline was injected into the ear marginal vein of the rabbits. Then, the tracer [$^{18}$F]HX-01 was injected, and the dosage was 0.5 mci/kg, and PET scanning was performed immediately as described in 1.4.2. On the second day, non-radioactive standard [$^{19}$F]HX-01 was injected through ear edge vein, and the dose of standard substance was 1 nmol/kg, that was dissolved in 2 ml normal saline. 30 min After injection of non-radioactive standard [$^{19}$F]HX-01, the tracer [$^{18}$F]HX-01 was injected, and the injection doe was 0.5 mCi/kg. After the injection, PET dynamic scanning was performed as described in 1.4.2. Meanwhile, PET, CT and PET/CT images were obtained by Syntgra fusion software. Using Compassview 5.0 to analyze and process the data, the brain, heart, liver, lung, kidney, bone and muscle of the region of interest (ROI) were drawn on the horizontal axis, and SUVmax was recorded.

1.2.3 Statistical Processin

The experimental data were represented as mean±standard deviation ($\chi$±SD), SPSS 21.0 statistical software was used to carry out the paired t-test.

2 Results

2.1 PET Dynamic Imaging of New Zealand Healthy White Rabbits

Seeing FIG. 8-11.

Figure 8:
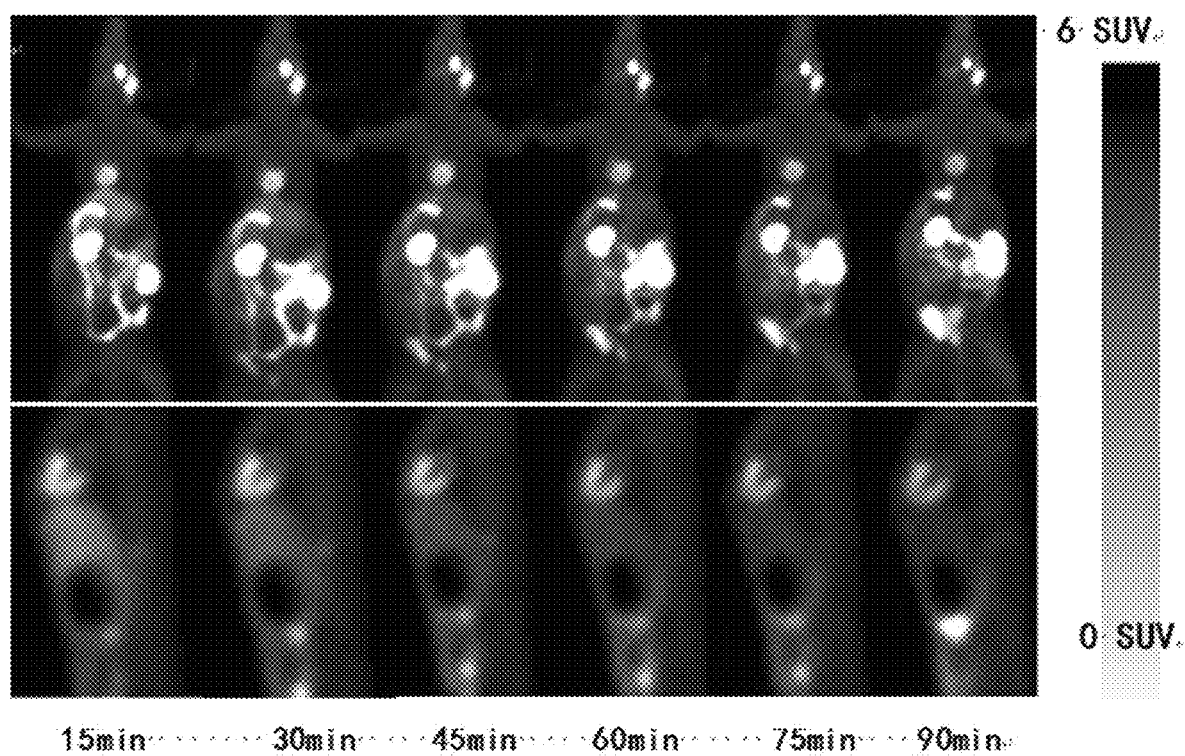
FIG. 8. Micro PET dynamic imaging after injection of [$^{18}$F]HX-01 in normal New Zealand white rabbits.
Figure 9:
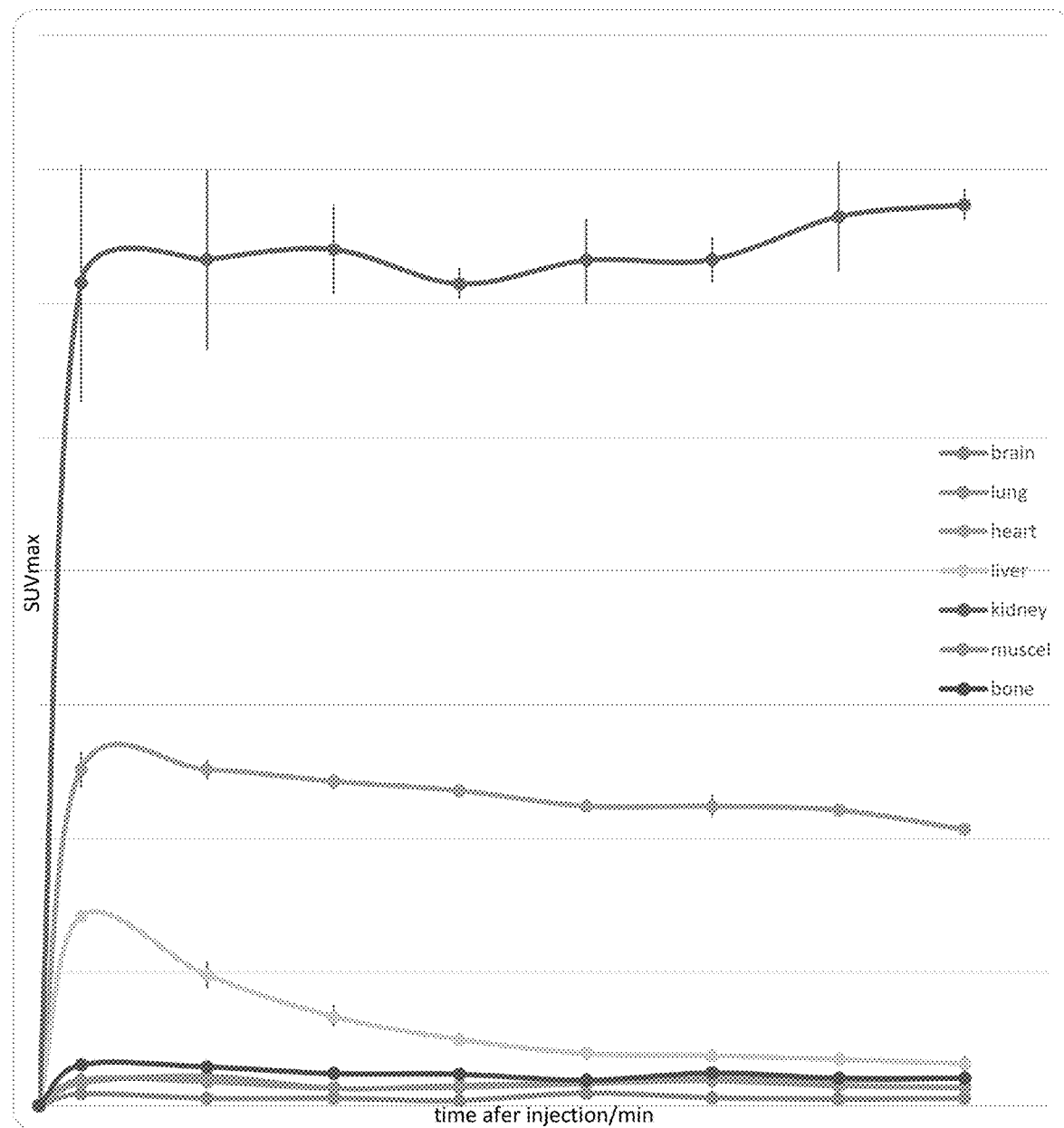
FIG. 9. Time-activity curves of various organs: SUVmax.

As shown in FIGS. 8-9, the rabbit's heart showed a uniform increase in radiation uptake, and as the elongation of time, the myocardial radiation uptake remained at a high level (within 2 h); at $5^{th}$ min and $110^{th}$ min, the myocardial SUVmax values were 5.03±0.27 and 4.13±0.02, respectively.

Figure 10:
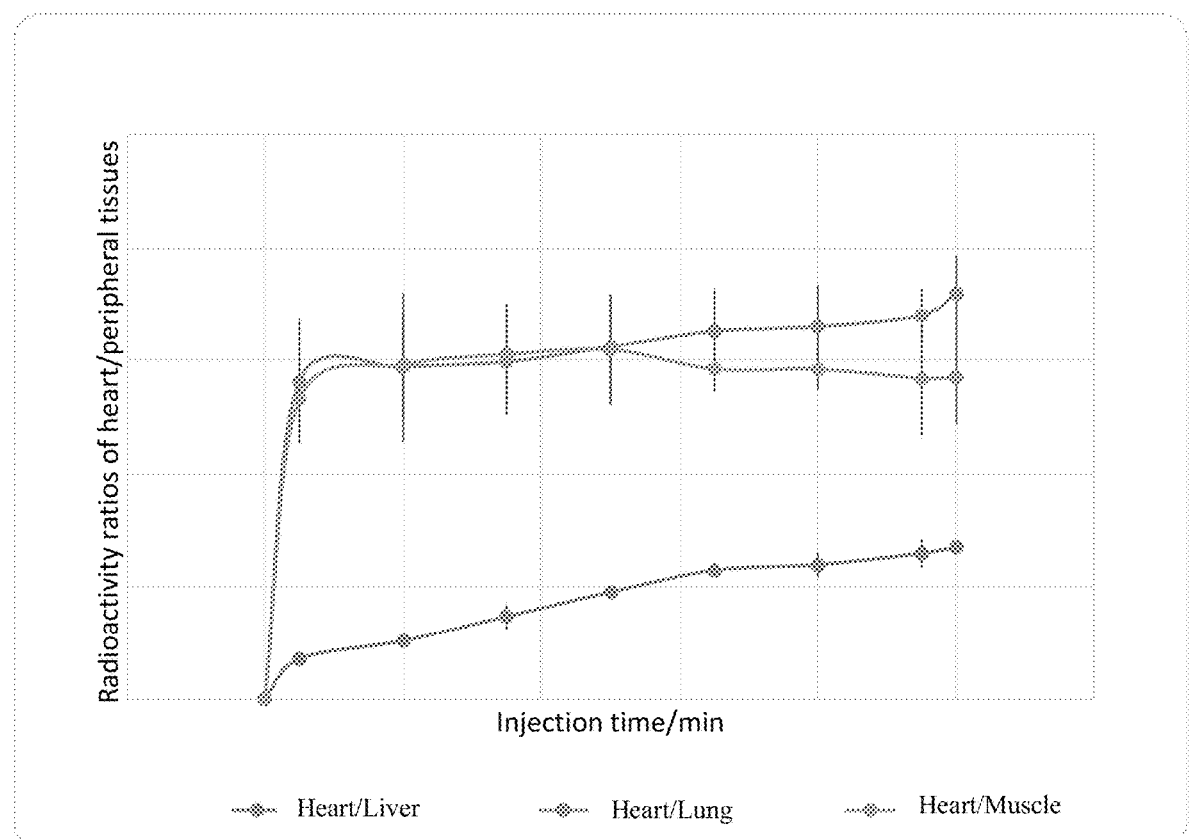
FIG. 10. SUVmax ratio of Heart/peripheral tissues within 2 hours after intravenous injection of [$^{18}$F]HX-01 in ear margin of normal New Zealand white rabbits.

At the beginning, the radioactivity uptake in liver was high, and the highest SUVmax value was 2.84±0.10 at 5 min. Then, the radioactivity gradually decreased as the extension of time. At 110 min, the SUVmax value of liver was 0.63±0.12, while the heart/liver radioactivity ratio increased significantly as the time, as shown in FIG. 10: for 5 min and 2 h, the values were 1.78±0.16 and 6.74±0.2, respectively, suggesting the metabolism of drug in liver.

The highest radiation uptake was found in the kidney. The SUVmax values of the kidney were 12.3±1.77 and 13.48±0.24 at 5 min and 2 h, respectively. As the development of time, radiation distribution and concentration gradually appeared in the bladder, suggesting that the drug was mainly excreted from the urinary system.

Figure 11:
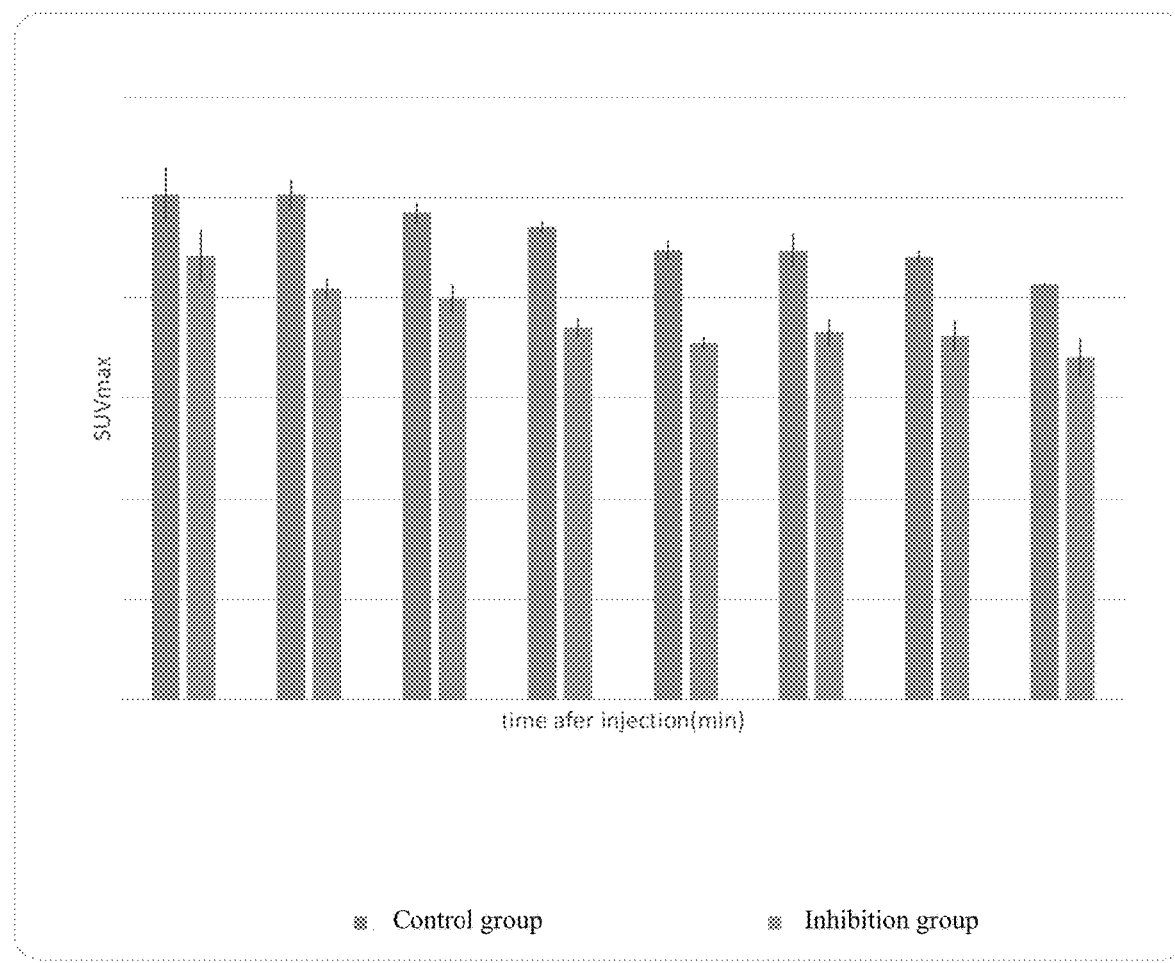
FIG. 11. Comparison of radioactivity in [$^{18}$F]HX-01 control group with that in [$^{19}$F]HX-01 inhibition group for cardiac uptake: SUVmax.

The intestinal tract also showed higher radioactivity, suggesting that part of the drug was excreted through the intestine. The uptake of [$^{18}$F]HX-01 in other tissues such as brain, lung, muscle and bone was extremely low (P<0.01), and as the progress of time, the radiation distribution did not have an obvious change. As shown in FIG. 11, the SUVmax ratios of heart/lung and heart/muscle were always greater than 10.

It could be seen that the myocardial uptake of [$^{18}$F]HX-01 was early, the uptake value was high, and the distribution is kept at a higher level for a long time (2 h). The drug was metabolized by liver and mainly excreted through the urinary system, and part of it was excreted through the intestinal tract. The radioactivity distribution in brain, lung, bone, muscle and other tissues and organs was extremely low.

Therefore, the $^{18}$F labeled berberine derivatives of the present invention had a myocardial targeting and good contrast of heart/surrounding tissues in New Zealand white rabbits.

2.2 Competitive Inhibition Test of [$^{18}$F]HX-01 and its Non-Radioactive Standard [$^{19}$F]HX-01

Figure 12:
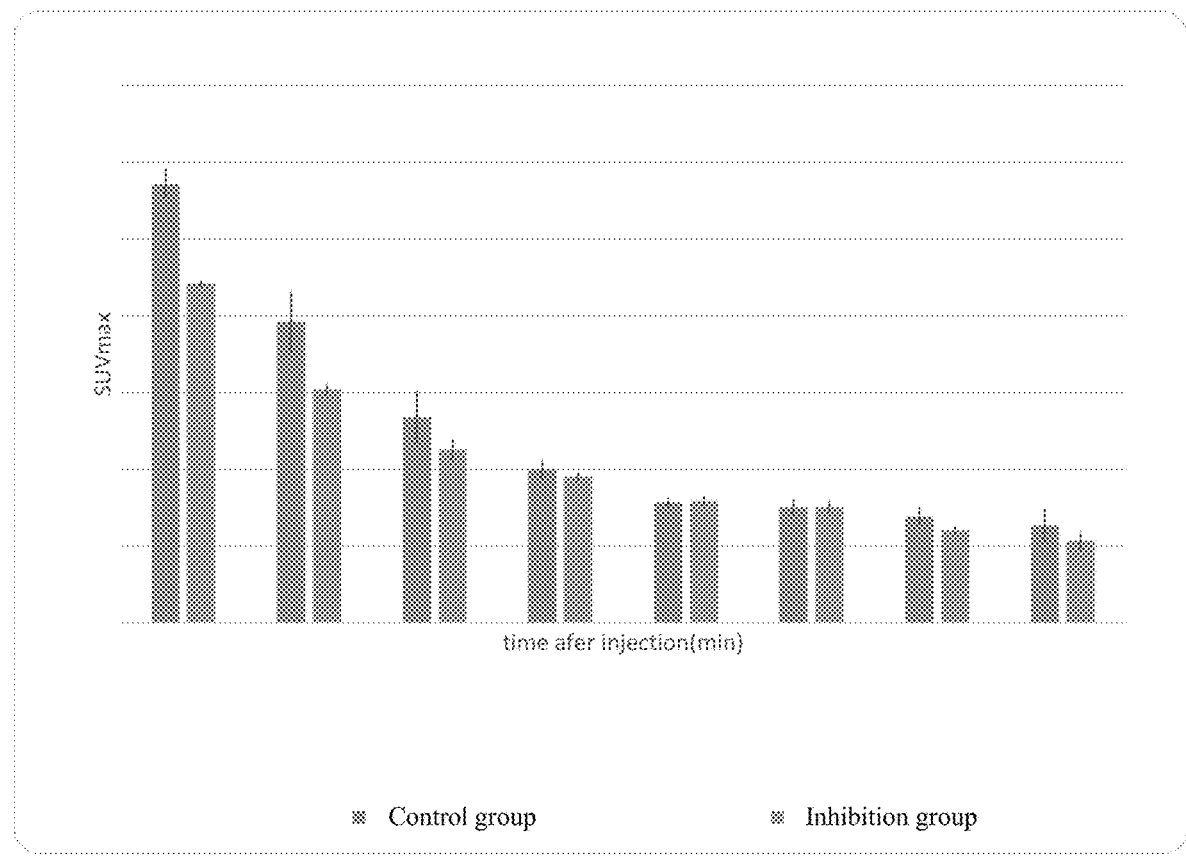
FIG. 12. Comparison of radioactivity in [$^{18}$F]HX-01 control group with that in [$^{19}$F]-HX-01 inhibition group for hepatic uptake: SUVmax.
Figure 13:
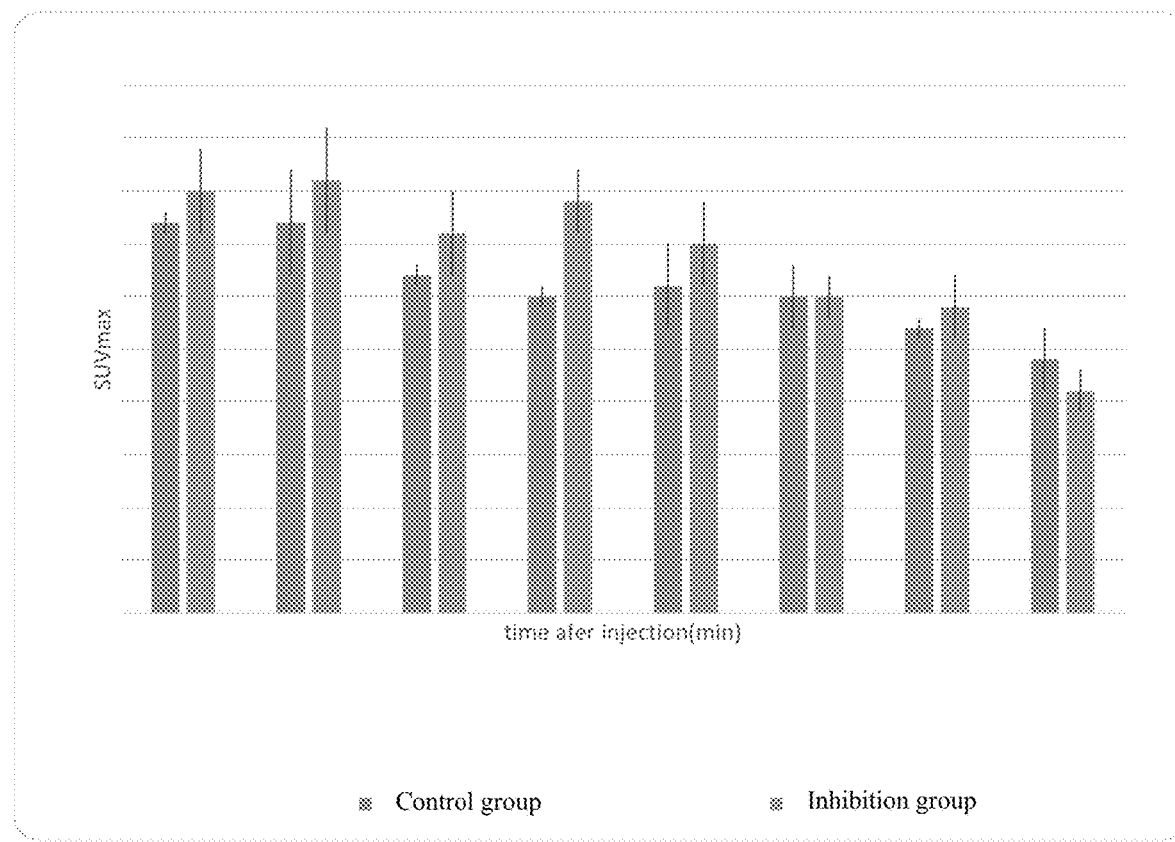
FIG. 13. Comparison of radioactivity in [$^{18}$F]HX-01 control group with that in [$^{19}$F]-HX-01 inhibition group for lung uptake: SUVmax.
Figure 14:
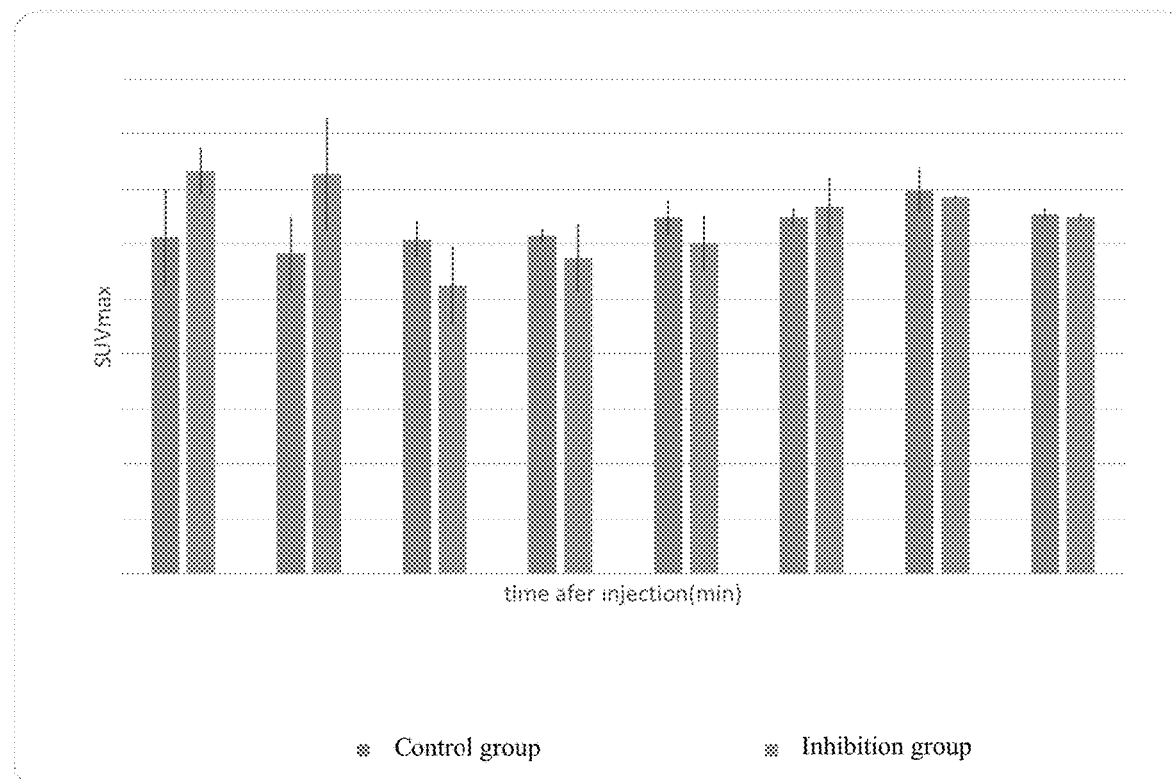
FIG. 14. Comparison of radioactivity in [$^{18}$F]HX-01 control group with that in [$^{19}$F]-HX-01 inhibition group for kidney uptake: SUVmax.

As shown in FIG. 11, the myocardial uptake of [$^{18}$F]HX-01 in the inhibition group injected with non-radioactive standard [$^{19}$F]HX-01 was lower than that in the control group, and SUVmax value was obviously reduced (P<0.001). FIG. 12 shows that the uptake of [$^{18}$F]HX-01 in liver gradually decreases as the progress of time, and there is no statistical significance between the inhibition group and the control group. FIG. 14 shows that the uptake of [$^{18}$F]HX-01 by kidney in the inhibition group and the control group was the highest, and there is no significant decrease as the elongation of time, and there is no statistical significance between the two groups. While the uptake of [$^{18}$F]HX-01 in lung (as shown in FIG. 13), bone, muscle, and brain tissue was all very low, and their SUVmax values were close to the background, which was an extremely low value. The difference between the inhibition group and the control group was not statistically significant (P>0.05).

Experimental Example 4 Micro PET Dynamic Imaging of $^{18}$F-Labeled Berberine Derivatives in Rat Myocardial Infarction Model 1 Experimental Materials and Methods
1.1 Experimental Materials
1.1.1 Experimental Reagents

[$^{18}$F]HX-01 was prepared by Department of Nuclear Medicin, Southwest Medical University. Physiological saline and penicillin were purchased from West China Hospital of Sichuan University.

1.1.2 Experimental Animals and Their Feeding Conditions
- Name: SD rats
- Grade: clean level
- Number: three rats for each group
- Gender: male
- Weight range: 200±20 kg
- Source: Chengdu Dashuo Experimental Animal Company purchased from Beijing Slake Biological Co., Ltd.; being raised in the Experimental Animal Center of Sichuan University.
- Environmental conditions: noise <60 dB; temperature 20-24° C.; humidity 40%-60%; good ventilation.
- Drinking water: the water quality is not lower than the urban drinking water standard.
- Feed: full nutrition pellet feed.

1.1.3 Apparatus

| Apparatus | Model | Manufacturer |
| --- | --- | --- |
| Radioactivity detector | FC3600 | Bioscan Company, USA |
| Micro PET scanner | SIEMENS Inveon MM | Siemens Company |
| Precision electronic balance | ESJ120-4 | Longteng Electronic Co., Ltd, Shenyang, China |
| Small animal ventilator | ALC-V8s type | Shanghai Alcott Biotechnology Co., Ltd. |
| Electrocardiograph | 6511 type | Shanghai Photoelectric Medical Electronic Instrument Co., Ltd. |
| Small animal anesthesia machine | LotNo. 11012VMR | Matrx Orchard Park New York, USA |

1.2 Experimental Method
1.2.1 Construction of Rat Myocardial Ischemia Model

After weighing the rat, a small animal anesthesia machine was used to maintain its anesthesia and carry out skin preparation, and the operation area was sterilized by iodine. A longitudinal incision was performed at the center of the neck and 1 cm above the sternum with a scalpel, and the layers were separated to expose the trachea. The 0th line was allowed to bypass the rear of the trachea for use. A small open was longitudinally cut between the 4th and 5th cartilage rings, and the sputum suction tube was used to remove bleeding and secretions, then a small animal tracheal intubation equipped by the ventilator was inserted and connected to the ventilator. The volume control mode was applied, with a tidal volume of 3 ml/100 g, respiration rate of 60-70 times/min, inhalation ratio of 1:1. The spare 0$^{th}$ line was tied to fix the tracheal intubation. After stabilization, a diagonal incision was cut from the lower right to the upper left of the left chest. The pectoral muscle and the third intercostal muscle were blindly separated layer by layer, and the 3-4 ribs was stretched, and the ribs was pulled with an arch and fixed. The pericardium was teared with tweezers, the heart was gently extruded, and then 2 mm below the junction of the pulmonary cone and the left atrial appendage, the proximal end of the left anterior descending branch was quickly sutured with 6-0 thread. The whitening of the anterior wall of the left ventricle and weakened movement and the electrocardiogram showing that the ST segment of the lead II was raised ≥0.1 mV/or the appearance of pathological Q waves were signs of successful ligation. The chest was immediately closed and a syringe was used to extract the chest gas to restore the negative pressure. The gauze was soaked with penicillin sodium and used to wipe the surgical area to prevent infection. After suturing the muscle layer and skin separately, the secretion of the oropharynx and airway was sucked up by the suction tube. Finally, the intubation was removed. Several chest compressions were done to help the rat to recover spontaneous breathing.

Model identification: the changes of electrocardiogram was recorded, and the anterior wall of left ventricle showed cyanosis or lead II ST segment arch dorsal lift greater than 0.1 mV and continued for more than 0.5 h were regarded as a sign of successful ligation.

1.2.2 MicroPET Dynamic Imaging of SD Rat Myocardial Infarction Model (0~420 min)

The myocardial infarction model of SD rat (n=3) was placed in the prone position, and the limbs were fixed to the scan panel with a strap. After the small animal anesthesia machine was used to maintain anesthesia, the tracer [$^{18}$F] HX-01 was rapidly injected intravenously through the tail vein of the SD rat myocardial infarction model, and the injection site was compressed for hemostasis. The injection dose was 350 μCi/rat. Heart collection: PET/CT breathing/heart-gated imaging of rat heart was performed, 3 beds. The first 30 min dynamic (8×5"+8×10"+3×40"+2×60"+2×120"+4×300"), 60 min, 90 min, 120 min and other time points are collected; CT of the diagnostic dose is used for organ identification and attenuation correction. After scanning and collection, Semis Micro PET scanner with analysis software was used to analyze and process the data, and the region of interest in the heart, liver, lung, blood pool and myocardial ischemic area was drawn. SUV of the region of interest was recorded, and T-A Curve was drawn.

2 Results
2.1 Micro PET Dynamic Imaging of SD Rat Myocardial Infarction Model, SUV Values of Main Organs, and Time-Activity Curve (30 min)

Figure 15:
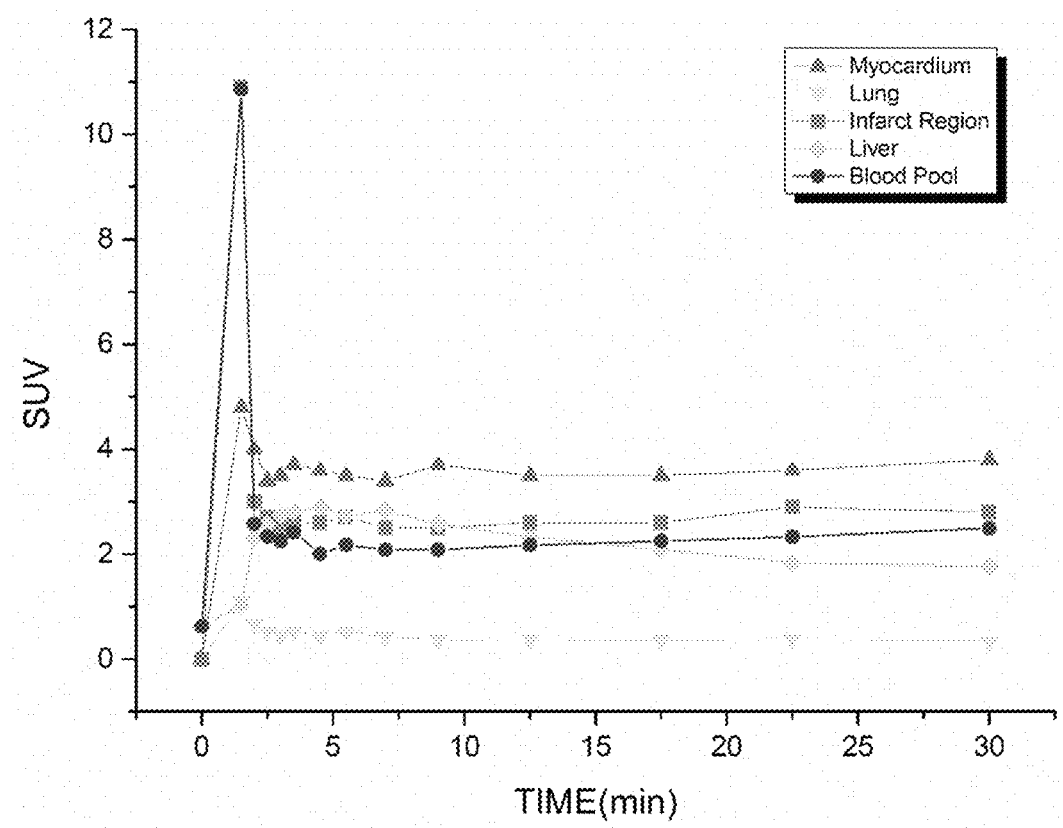
FIG. 15. Time-activity curve (30 min) for SUV values of major organs in SD rat myocardial infarction model by Micro PET dynamic imaging.

As shown in FIG. 15, the uptake of [$^{18}$F]HX-01 by heart of SD rat was early, and the uptake value was the highest, and a constant distribution in the myocardium was observed within 30 minutes after injection. At 4 min, 8 min, 18 min, 30 min after injection, SUVmean values of the left ventricular myocardium were 3.6, 3.7, 3.5, and 3.8, respectively. The radioactivity distribution in the lung was very low, showing a background curve. The SUVmean values of lung were 0.43, 0.37, 0.36, and 0.35, respectively. The early uptake of imaging agents by liver was higher, but lower than that of myocardium. At 4 min, 8 min, 18 min, and 30 min after injection, the SUVmean values of liver were 2.8, 2.4, 1.8, and 1.4, respectively. The contrast degree of heart/liver was significantly enhanced; the radioactivity in the myocardial infarction area is constantly distributed. At 4 min, 8 min, 18 min, and 30 min after injection, the SUVmean values in the myocardial infarction area were 2.6, 2.5, 2.6, and 2.8, respectively. The blood pool image showed that the radioactivity distribution in blood was significantly lower than that in the myocardium, and at 4 min, 8 min, 18 min, 30 min after injection, SUVmean values of blood pool were 1.7, 1.8, 2, and 2.3, respectively.

2.2 Micro PET Dynamic Imaging of SD Rat Myocardial Infarction Model (0~420 min)

Figure 16:
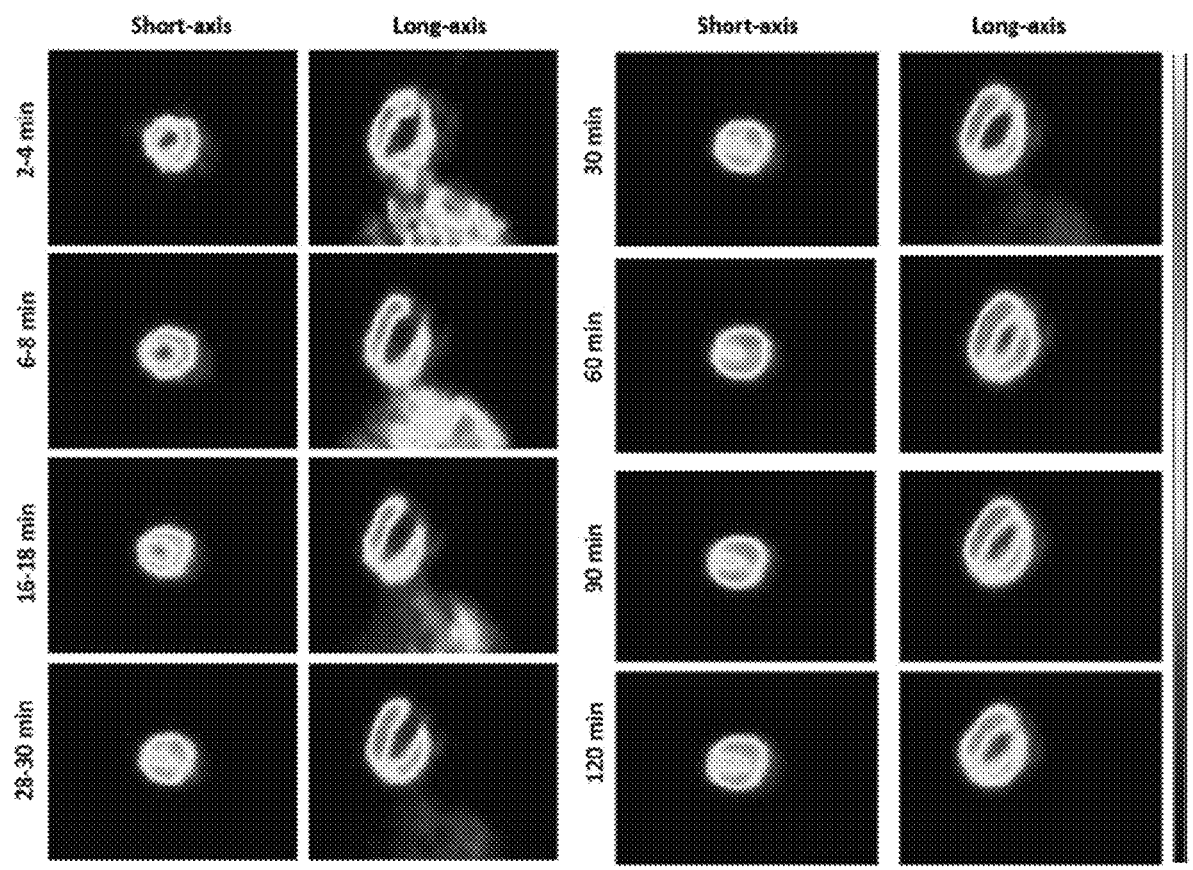
FIG. 16. Micro PET dynamic imaging for SD rat myocardial infarction model (0~120 min). 2-4 min after injection, the left ventricular myocardial contour is clearly visible, and in the anterior wall of the left ventricle near the apical region, the radiological defect can be seen, and the liver shadow is thicker. Subsequently, the radioactivity distribution in the myocardium was constant, and the radioactivity distribution in the liver was rapidly reduced. By 30 min, a high contrast image of heart vs peripheral tissue has been obtained and kept for 120 min. A fixed radioactive defect area is seen in the anterior wall of the left ventricle near the apical region.

As shown in FIG. 16, myocardial uptake of [$^{18}$F]HX-01 was early, and the uptake value was the highest. 30 minutes after injection, it could be seen that the drug was quickly cleared from the liver. At 30 minutes, a high contrast image of myocardial/surrounding tissues was obtained and lasted for 120 minutes. The anterior wall of left ventricle near apical area showed a fixed radioactive defect. 30 min, 60 min, 90 min, 120 min after injection, SUVmean values of left ventricular myocardium were 3.8, 3.7, 3.7, and 3.6, respectively; SUVmean values of liver were 1.4, 0.73, 0.52, and 0.51, respectively; SUVmean values of lung were 0.34, 0.30, 0.30, and 0.29, respectively; SUVmean values of blood pool were 2.3, 2.1, 2.1, and 2, respectively; SUVmean values of myocardial infarction area were 2.8, 2.8, 2.8, and 2.7, respectively. 30 min, 60 min, 90 min, 120 min after injection, the ratios of heart/liver, heart/lung, heart/blood pool were 30 min (2.71, 10.99, and 1.65), 60 min (5.06, 12.38, and 1.76), 90 min (7.11, 12.40, and 1.76), 120 min (7.10, 12.58, and 1.8), respectively.

In summary, $^{18}$F-labeled berberine derivatives of the present invention had ideal characteristics of myocardial targeting distribution and pharmacodynamics. Myocardial uptake is early and the uptake value is high. The rat heart can be clearly visualized 4 minutes after injection, and the drug was cleared from the liver in 30 minutes. It distributed constantly in the myocardium. 30 minutes after injection, high contrast images of heart/peripheral tissues (heart/liver, heart/lung, heart/blood, etc.) could be obtained, and the drug remained in the myocardium for 2 h. 4~120 min after injection, the radioactive defect area was fixed in the anterior wall of the left ventricle near the apical area (myocardial infarction area). $^{18}$F-labeled berberine derivatives could be used as good PET myocardial perfusion imaging agents, with good application prospects.

In summary, $^{18}$F-labeled berberine derivatives of the present invention had good characteristics of myocardial targeting distribution, and the contrast values of heart/peripheral tissues (liver, lung, blood, muscle, bone, etc.) were high, that could be used as good PET myocardial perfusion imaging agents, with good application prospects.

The invention claimed is:

1. A method for myocardial perfusion imaging, comprising:
    intravenously injecting a compound comprising a berberine derivative to a subject in need thereof; and
    carrying out myocardial perfusion imaging of the subject, wherein the berberine derivative is radiolabeled with $^{18}$F and has a structural formula of

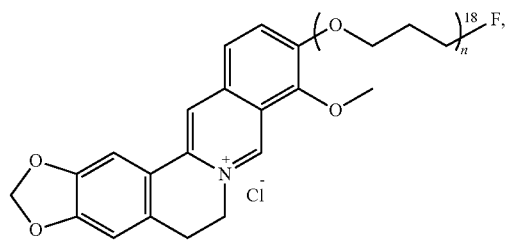

wherein n=2 or 3.

2. The method according to claim 1, wherein the myocardial perfusion imaging is carried out between 30 minutes to 2 hours after the injecting step.

3. A method for diagnosing a coronary heart disease, comprising:
    intravenously injecting a compound comprising a berberine derivative to a subject in need thereof; and
    carrying out myocardial perfusion imaging of the subject, wherein the berberine derivative is radiolabeled with $^{18}$F and has a structural formula of

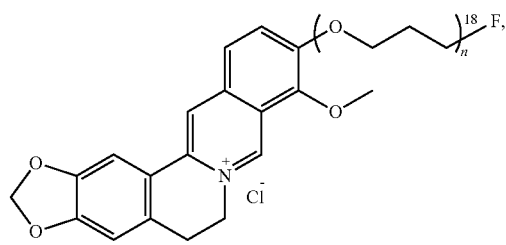

wherein n=2 or 3.

4. The method according claim 3, wherein the myocardial perfusion imaging is carried out between 30 minutes to 2 hours after the injecting step.

* * * * *